(12) United States Patent
Sutty et al.

(10) Patent No.: US 12,251,257 B2
(45) Date of Patent: Mar. 18, 2025

(54) SYSTEM AND METHOD FOR ANALYZING BREAST SUPPORT ENVIRONMENT

(71) Applicant: GE Precision Healthcare LLC, Wauwatosa, WI (US)

(72) Inventors: Jerome Sutty, Verrières le buisson (FR); Laurence Vancamberg, Poissy (FR); Vincent Croulard, Magny en Vexin (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 192 days.

(21) Appl. No.: 17/968,932

(22) Filed: Oct. 19, 2022

(65) Prior Publication Data

US 2024/0130705 A1    Apr. 25, 2024
US 2024/0225586 A9    Jul. 11, 2024

(51) Int. Cl.
*A61B 6/00*    (2024.01)
*A61B 6/02*    (2006.01)
(Continued)

(52) U.S. Cl.
CPC .............. *A61B 6/547* (2013.01); *A61B 6/025* (2013.01); *A61B 6/0414* (2013.01);
(Continued)

(58) Field of Classification Search
CPC ....... A61B 6/547; A61B 6/025; A61B 6/0414; A61B 6/0435; A61B 6/502; A61B 10/02;
(Continued)

(56) References Cited

U.S. PATENT DOCUMENTS

2016/0183889 A1*  6/2016  Matsuura ................. A61B 6/54
                                                      378/37
2020/0060632 A1   2/2020  Blaski et al.
(Continued)

FOREIGN PATENT DOCUMENTS

EP         0936889        *  7/2010

OTHER PUBLICATIONS

EP application 23201330.0 filed Oct. 2, 2023—Search report issued Mar. 7, 2024; 9 pages.

*Primary Examiner* — Alexei Bykhovski
(74) *Attorney, Agent, or Firm* — Boyle Fredrickson S.C.

(57) ABSTRACT

According to one aspect of an exemplary embodiment of the disclosure, an imaging device or system, e.g., a mammography imaging system or device, includes a distance and location sensing system on the imaging system/e to provide accurate distance and position information from one or more sensing device(s) constituting the system that measure the elapsed time between the emission of the wave or radiation from the sensing device and the detection of the reflected wave or radiation. Examples of the types of sensing devices include ultrasound sensing devices, MEMS radar devices and time-of-flight (ToF) sensing devices. The distance information can be employed to determine the relative positions to produce a distance map illustrating the position and shape of any objects sensed within the zone by the sensing device(s), to determine the rate of change of the positions, i.e., the speed, of the objects relative to one another for use in controlling movement of various components of the imaging system, and to determine the shape of the object and changes in the shape of the object.

20 Claims, 11 Drawing Sheets

(51) Int. Cl.
*A61B 6/04* (2006.01)
*A61B 6/50* (2024.01)
*A61B 10/02* (2006.01)

(52) U.S. Cl.
CPC ............ *A61B 6/0435* (2013.01); *A61B 6/502* (2013.01); *A61B 10/02* (2013.01); *A61B 2562/0247* (2013.01)

(58) Field of Classification Search
CPC ........ A61B 2562/0247; A61B 10/0233; G01S 17/894
See application file for complete search history.

(56) References Cited

U.S. PATENT DOCUMENTS

| | | | |
|---|---|---|---|
| 2021/0045700 A1* | 2/2021 | St. Pierre | A61B 6/502 |
| 2021/0153831 A1* | 5/2021 | Kobayashi | A61B 6/502 |
| 2021/0298702 A1* | 9/2021 | Konno | A61B 6/502 |
| 2022/0192614 A1* | 6/2022 | Vancamberg | A61B 6/4458 |
| 2023/0005149 A1* | 1/2023 | Nakayama | G06T 7/90 |

* cited by examiner

SYSTEM AND METHOD FOR ANALYZING BREAST SUPPORT ENVIRONMENT

FIELD OF THE DISCLOSURE

The present disclosure relates generally to medical imaging systems, including mammography systems and devices, and more specifically to patient and device location systems utilized with a medical imaging device.

BACKGROUND OF THE DISCLOSURE

Embodiments of the invention relate generally to X-ray medical imaging, and more particularly to devices, systems and methods employed to perform various imaging procedures, such as mammography imaging procedures including but not limited to spectral mammography (SM), such as 2D/3D dual-energy contrast-enhanced (CE) mammography exams, full-field digital mammography (FFDM) or digital breast tomosynthesis (DBT) mammography exams.

Spectral mammography (SM) is an X-ray imaging modality used to scan breasts for screening, diagnosis and/or interventional examinations. The effectiveness of spectral mammography is affected by numerous factors, one of which is the two-dimensional (2D) rendering of images obtained using SM.

Alternative systems to SM are also known for breast imaging. Some examples include full-field digital mammography, which captures the image directly onto a flat-panel detector, computed radiography, which involves the use of a cassette that contains an imaging plate), or digital breast tomosynthesis (DBT). A digital breast tomosynthesis (DBT) or mammography-tomography (mammo-tomo) system is a dedicated mammography system that acquires several (e.g., tens of) angularly offset projection X-ray images and uses the resulting X-ray image data to reconstruct three-dimensional (3D) image datasets.

The 3D image datasets are used to form various volumetric representations of the imaged breast, including an entire 3D volume of the breast, and various 3D sections of the 3D volume, such as slices or slabs constituting specified thicknesses of the 3D volume oriented to provide the desired view of one or more regions of interest (ROI) detected within the 3D image dataset.

In addition, when the 3D image datasets of the breast have been produced, after being utilized in a suitable diagnosis procedure, they can be utilized to guide a biopsy device employed with the DBT system into the breast to obtain a biopsy of the region of interest (ROI) identified within the 3D image datasets. In DBT systems, the biopsy device is disposed directly on the DBT system in order to be able to perform the biopsy utilizing the 3D image dataset to guide the biopsy device to the ROI.

With regard to the use of mammography devices, the process of obtaining high quality mammographic images from breast tissue requires a technician to position the breast of a patient between one or more paddles that compress the breast in order to immobilize and flatten it during image acquisition. The compression force applied to a breast improves image quality by reducing the thickness of the breast while spreading the breast tissue over a larger area; this facilitates interpretation of obtained imagery since the amount of overlying tissue for structures within the imaged breast is minimized.

Reduction of the breast thickness by compression is also important in managing patient radiation dosage. In general, the thicker the compressed breast, the more x-ray attenuation. Therefore, a higher x-ray dosage is necessary when imaging thicker breast tissue as compared to the dosage required for thinner tissue. While greater compression forces are desirable for obtaining clear images with lower radiation dosages, greater compression forces may contribute to patient pain or discomfort. Such patients may not schedule or may delay any future examinations due to the fear of an uncomfortable procedure, thereby possibly increasing the risk that a serious medical condition may not be detected in a timely fashion.

In many diagnostic mammography imaging devices, such that disclosed in US Patent Application Publication No. US20200060632, entitled *Apparatus And Method For Mammographic Breast Compression*, the entirety of which is expressly incorporated herein by reference for all purposes, the compression of the breast on the mammography imaging device is controlled by the technician using a footswitch with a binary positioning system, i.e., the footswitch is moveable between an "on" position to cause movement of the compression paddle(s) and an "off" position where the compression paddle(s) are stationary. When the footswitch is on the "on" position, the paddle(s) is moved towards the breast under the full operational speed of the motor operably connected to the paddle(s) until contact of the paddle(s) with the breast is detected.

The contact between the paddle and the breast is detected in various manners, including the view of the technician seeing the paddle contacting and compressing the breast and/or through the use of various systems such as, for example, force sensors disposed on the paddle or other breast-contacting surface that measure the force applied to the breast to maintain the compression forces below certain predetermined thresholds. Depending on the patient, however, even compression forces below predetermined thresholds may cause pain or discomfort.

In addition, as the movement of the paddle towards the breast prior to contact with the breast is at a relatively high rate of speed, which can create unease in the patient upon viewing the fast movement of the paddle, on many occasions due to the delay in reaction by the technician controlling the movement of the paddle via the footswitch and/or the detection by force sensors of the contact of the paddle with the breast, the speed of the paddle upon contact with the breast can create compressive forces on the breast that exceed the predetermined threshold. Further, though the technician can attempt to avoid this by incrementally using the footswitch, the delay can still cause the paddle to contact the breast at a higher rate of speed than desired. Though this initial high compressive force on the breast is normally short in duration, as they are detected by the technician and/or force sensor shortly after initial contact of the paddle with the breast, with the speed of the paddle being quickly reduced or stopped, the initial contact can result in pain or discomfort to the patient.

Furthermore, either just prior to or after the paddle is moved into initial contact with the patient, the movement of the paddle is controlled in a finer manner by the technician to slowly achieve a desired compression force on the breast for optimal imaging of the breast. In performing this more closely controlled, finer movement of the paddle, the technician employs the footswitch to move the paddle, but by activating the footswitch in successive short intervals or periods of time to incrementally move the paddle towards the breast and reach the target compressive force to eb exerted on the breast. In addition to, or alternatively to the footswitch, the mammography imaging device may include a fine movement adjustment knob. Rotation of the knob by the technician causes the paddle to move towards or away from the breast in a finer manner than the footswitch to more accurately position the paddle against the breast to achieve the desired compressive force on the breast.

However, even though the footswitch and/or knob can be operated by the technician to more finely control the movement of the paddle to contact the breast with the desired compressive force, there still remains the issue of accurately detecting the force exerted on the breast during movement of the paddle to attempt to minimize any unnecessary pain or discomfort to the patient. In the case of the technician viewing the breast as it is compressed by the paddle, the estimation of the compression force provided by the paddle on the breast is subjective at best and depends greatly on the experience level of the technician in the operation of the mammography imaging device. Additionally, even when the mammography imaging device includes force sensors on the paddle and/or detectors to provide a more objective indication of the compressive force being exerted on the breast, this sensed value can vary based on breast shape, such that the same force exerted on different breasts can result in different compressions and resulting mammography images.

Another significant issue with prior art mammography devices involves the proper positioning of the breast within the field of view (FOV) of the mammography imaging device in order to obtain the desired images of the breast. More specifically, with regard to most mammography devices, the parameters that need to be addressed with regard to breast positioning include: 1) locating the breast accurately on the breast support/detector, 2) matching the size of the paddle employed for a given imaging procedure to the size of the breast being imaged, and 3) the location of the breast on the support/detector must avoid positioning of the arm of the patient within the FOV for the mammography imaging device, among others. If any one or more of these imaging parameters are not met prior to initiation of the imaging procedure, the images will not have desired quality and/or will not cover the desired area of the breast, such that the images must be retaken in a subsequent imaging procedure, consequently requiring an additional radiation dose to the patient, which is highly undesirable.

The positioning of the breast with regard to the detector also creates issues concerning the identification of the breast being fluoroscopically or digitally imaged. Even if a breast is properly disposed on the support to provide the desired compression by the paddle for optimal images of the breast, the resulting fluoroscopic or digital images or 3D image dataset of the breast does not provide any indication with regard to the laterality of the breast, i.e., whether the breast is the left breast or the right breast. Thus, unless the technician enters the appropriate information regarding the laterality of the breast being imaged, it is difficult if not impossible to determine the laterality of the imaged breast from the images or 3D image dataset. This results in the requirement for a subsequent imaging procedure which in undesirable for the reasons of increased radiation dose to the patient, and increased time and expense in providing any diagnosis for the patient, among others.

For the implementation of the mammography imaging device in a biopsy procedure, after obtaining the fluoroscopic or digital images or the 3D image dataset, the results of the analysis and/or diagnosis of the images of 3D image dataset are used to obtain the location(s) of the breast tissue to be biopsied while the breast is still positioned on the mammography imaging device. In the biopsy procedure, sample images of the breast can be obtained to confirm the presence of the ROIs e.g., microcalcifications, in the tissues being biopsied while the patient breast is still on the breast support and prior to the actual performance of the biopsy procedure. In current mammography imaging devices, the technician will manually adjust the collimator relative to the ROIs such that the radiation for the sample images is directly specifically at the area(s) containing the ROIs to prevent the remainder of the breast from receiving any unnecessary radiation.

However, as the collimator is manually adjusted by the technician, errors can readily occur in the positioning of the collimator, such that images of less than the areas containing the ROIs or completely omitting the areas containing the ROIs can be obtained, requiring additional imaging processes.

To address these shortcomings of prior art medical imaging devices, and in particular mammography imaging devices, cameras have been employed in certain imaging devices as a vision detection system to provide the location of the various components of the imaging system and the patient relative the imaging system. In these imaging systems, such as that disclosed in US Patent Application Publication No. US2022/0192614, entitled Vision-Guided Biopsy System And Method For Mammography, the entirety of which is expressly incorporated herein by reference for all purposes the vision system operates to determine the position of the robotic arm, such as the last segment of the robotic arm or the end effector, or of a biopsy tool and/or the biopsy needle tip mounted to the end effector, as well as to control the movement/operation of the biopsy system, such as at the final end-pose or pre-firing position of the biopsy device to perform the biopsy procedure. The vision system utilizes one or more cameras to visually determine the position the robotic arm, e.g., one of the segments of the robotic arm such as the end effector, or the biopsy device or the biopsy device needle within the required tolerances for the biopsy procedure. The v at least one camera is capable of determining and providing information to the imaging system regarding the exact location of one or more of the different segment(s) of the robotic arm, such as the end effector, the biopsy device and/or the tip of the needle forming a part of the biopsy device relative to the mammography system, as well as to the ROI determined within the fluoroscopic or digital images or 3D image dataset reconstructed from the X-ray image data obtained by the imaging system. The placement of the camera provides an optimal field of the view for the vision system of the end effector and optionally the patient breast, such as for collision management, while also accommodating for the presence of other components of the mammography system and obstructions, such as the technician and patient, among others. By visually ascertaining the location of the end effector using the camera at the initial localization of the end effector, and optionally through the movement of the end effector to the pre-firing position, the biopsy guidance system can use this visual determination from the camera to precisely locate and guide the position of the end effector and the patient breast, including the desired ROIs disposed within the breast that are to be biopsied, within the required tolerance (e.g., +/−1 mm) for the biopsy procedure.

While the use of the camera provides the imaging system with accurate position information on the various components of the imaging device as well as the patient, there are also certain issues with regard to the use of cameras as the vision system for the imaging device. In particular, the camera requires a significant amount of power for its operation, often necessitating an additional power connection or power source for the video camera.

Further, in order to integrate the camera with the imaging system to provide the location information to the imaging system, there is a significant amount of hardware and software required to be added to the imaging system to provide the necessary connections for the operation of the camera vision system in conjunction with the imaging system. These connections consequently increase the complexity and cost of the imaging system.

In addition, as the camera records images in the visible spectrum to produce the vision guidance information for use by the imaging system, the lighting in the area or room where the imaging system incorporating the camera vision system is operated must be modified to enable optimal operation of the camera vision system. In particular, the camera requires sufficient light around the imaging system to produce the images, which can require a higher level of ambient light to adequately illuminate all of the portions of the imaging device and the patient than otherwise would be employed.

Finally, as many imaging procedures, and mammography imaging procedures in particular require the patient to be in at least a partial state of undress, the use of a camera to obtain images of the patient is often viewed as undesirable from the patient perspective.

Therefore, with regard to each of the aforementioned shortcomings of prior art imaging systems concerning the ability of those imaging systems to provide and utilize location information concerning components of the imaging system and the patient being imaged in the control of the imaging system, it is desirable to develop an improved system and method for the operation of the mammography imaging device that more accurately determine the position of the imaging system and the patient to more accurately control the operation of the imaging system and provide increased comfort to the patient being imaged.

SUMMARY OF THE DISCLOSURE

According to one aspect of an exemplary embodiment of the disclosure, an imaging device or system, e.g., a mammography imaging system or device, includes a distance and location sensing system on the imaging system/e to provide accurate distance and position information from one or more sensing device(s) constituting the system, a variety of benefits in relation to prior art vision detection and location systems are achieved. Initially, the sensing device(s) employed in the distance and location sensing system are much less complex in construction and operation than the cameras utilized in prior art vision systems. In an exemplary embodiment, the sensing devices only measure the elapsed time between the emission of the wave or radiation from the sensing device and the detection of the reflected wave or radiation. Examples of the types of sensing devices include ultrasound sensing devices, MEMS radar devices and time-of-flight (ToF) sensing devices. As such, the structural components required for the sensing device to function are much less complex and less costly than for video and still cameras. Further, the distance data, in the form of the elapsed time between emission and detection, is significantly easier to use computationally to arrive at the distance data supplied to the controller for controlling the operation of the various components of the imaging system/device. as a result of the simpler construction and data complexity of the sensing device(s), the distance and location sensing system incorporating the sensing device(s) can be integrated into existing and new imaging systems/devices in a much easier and less costly manner.

In addition, these types of sensing devices are capable of covering a zone encompassing an expanded area spaced from the emission area of the sensing device, such that a number of different points within the zone can be simultaneously sensed by the sensing device to determine the presence and distance of one or more objects from the sensing device. This distance information can be employed by the sensing device or a controller/central processing unit operable connected to the sensing device(s) to determine the relative positions to produce a distance map illustrating the position and shape of any objects sensed within the zone by the sensing device(s). In addition, the position information can be obtained by the sensing devices during the operation of the imaging system in order to determine the rate of change of the positions, i.e., the speed, of the object relative to one another for use in controlling movement of various components of the imaging system.

Further, the information obtained regarding the shape of the object being imaged can also be determined as the shape of the object changes, e.g., the change in shape of a breast upon compression between a compression plate and a detector surface, to estimate the pressure exerted on the object, with or without the accompanying use of a separate force sensor.

Further, the use of the waves and radiation emitted by the sensing device to obtain the distance data are much less susceptible to interference from ambient light conditions, as is the case with cameras which require significant ambient light to adequately capture the required visible spectrum images and/or video.

Finally, from the standpoint of patient comfort, the distance and location sensing system does not record any images and/or video of the patient in any state of undress due to the manner in which the distance data is obtained, i.e., through the use of reflected waves and radiation, rather than visible spectrum images or video. Thus, the entire lack of any images of any type of the patient in a state of undress during the entire imaging and biopsy procedure greatly reduces any patient anxiety with regard to the performance of the imaging and biopsy procedures utilizing the imaging system employing the distance and location sensing system.

According to still another aspect of an exemplary embodiment of the present disclosure, a mammography system includes a gantry including radiation source, a detector alignable with the radiation source, and a compression paddle moveable relative to the detector to secure a patient breast therebetween, a controller operably connected to the gantry to control the operation of the radiation source and detector to generate image data, the controller including a central processing unit and interconnected database for processing the image data from the detector, a display operably connected to the controller for presenting information to a user, and a user interface operably connected to the controller to enable user input to the controller and a distance and location system disposed on the gantry and operably connected to the controller, the distance and location system including at least one sensing device operable to generate distance data regarding the breast disposed on the detector and to guide the movement of the compression plate to compress the breast on the detector.

According to still another aspect of an exemplary embodiment of the present disclosure, a method for determining the relative distance between an object to be imaged and one or more components of an imaging system includes the steps of providing an imaging system having a gantry disposed movably disposed on a support surface and including a radiation source, a detector alignable with the radiation source, the detector having a surface on which an object to be imaged is adapted to be positioned, a controller operably connected to the gantry to control the operation of the radiation source and detector to generate image data in an imaging procedure performed by the imaging system, the controller including a central processing unit and interconnected database for processing the image data from the detector to create images, a display operably connected to the controller for presenting information to a user, and a user interface operably connected to the controller to enable user input to the controller and a distance and location sensing system disposed on the gantry and operably connected to the controller the distance and location system including at least one sensing device operable to generate distance data concerning the object, positioning the object on the surface between the radiation source and the detector, operating the at least one sensing device to obtain distance data regarding the distance of the object from the at least one sensing device, determining a position of the object on the surface to determine the position of the object relative to the surface, and optionally adjusting the operation of one or more components of the imaging system based on the position of the object on the surface.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Further, while the embodiments disclosed herein are described with respect to a mammography apparatus for the 2-dimensional imaging of breast tissue, it is to be understood that embodiments of the invention may be applicable to other types of imaging devices for both 2-dimensional and 3-dimensional imaging including, for example, fluoroscopy, full-filed digital mammography, digital breast tomosynthesis (DBT) and spectral mammography (single or multi-energy), as well as for imaging procedures for tissue other than breast tissue. Further still, embodiments of the invention may be used to analyze tissue, generally, and are not limited to analyzing human tissue.

Figure 1:
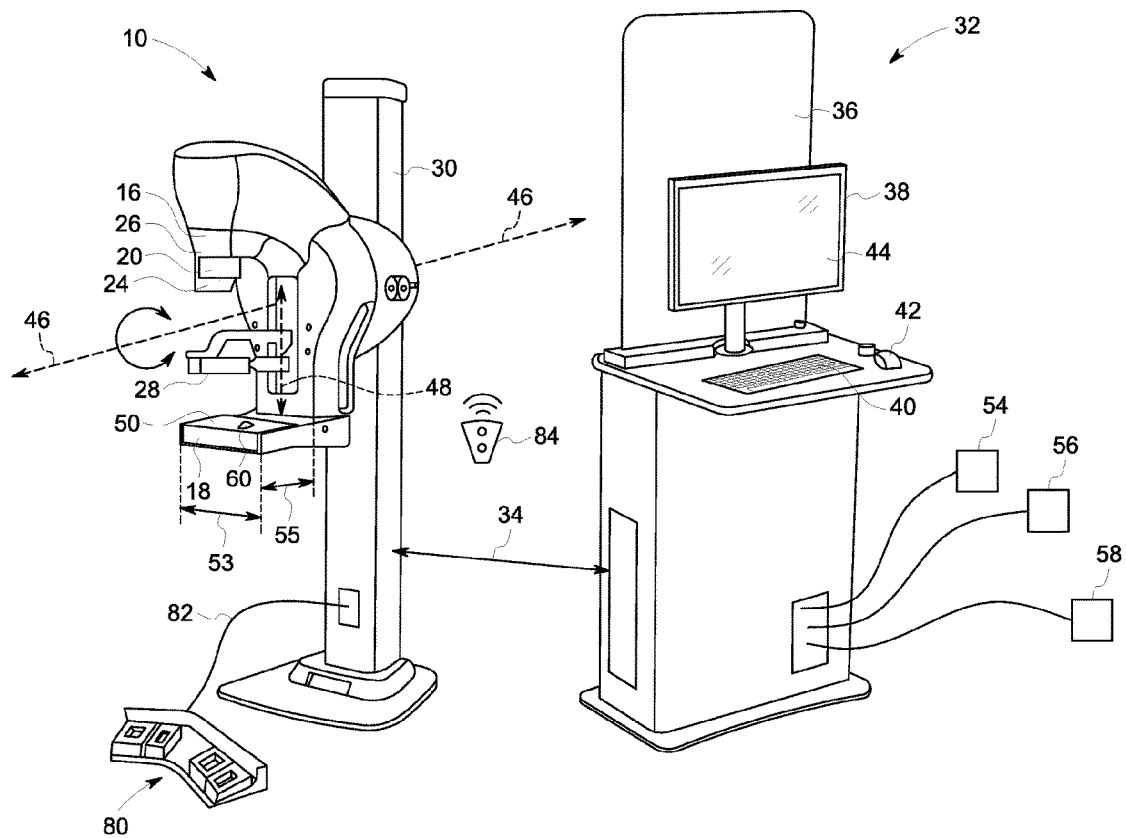
FIG. 1 is a perspective view of an imaging device in the form of a mammography apparatus for imaging the breast tissue of a patient, in accordance with an embodiment of the disclosure.
Figure 2:
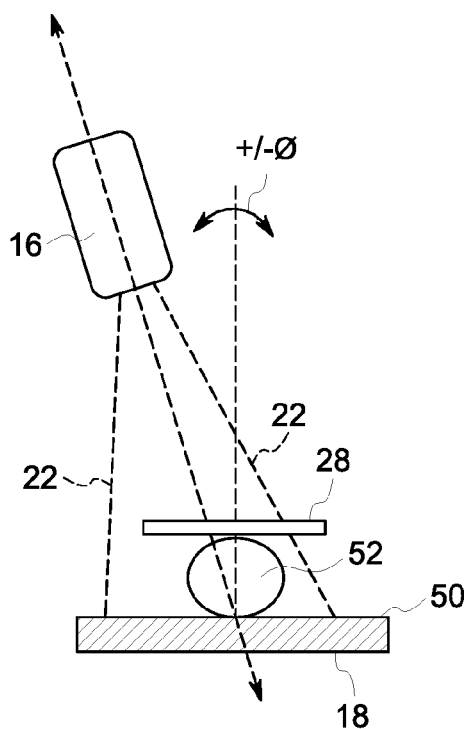
FIG. 2 is a diagram of the system of FIG. 1, showing the radiation source of the system in a scanning position, in accordance with an embodiment of the disclosure.

Referring now to FIGS. 1 and 2, the major components of an exemplary imaging system 10 formed as a mammography system 12 for imaging breast tissue according to an embodiment of the invention are shown. The system 10, such that disclosed in US Patent Application Publication No. US20200060632, entitled *Apparatus And Method For Mammographic Breast Compression*, the entirety of which is expressly incorporated herein by reference for all purposes, includes a radiation source/x-ray source 16, a radiation detector 18, and a collimator 20. The radiation source 16 is movable between a variety of imaging positions relative to the detector 18, and is operative to emit radiation rays 22 (FIG. 2) that are received by the radiation detector 18 to provide an image of a breast 52. In embodiments, the system 10 may include a patient shield 24 mounted to the radiation source 16 via face shield rails 26 to prevent the patient's head from obstructing the radiation rays and protecting the patient from the radiation rays 22.

Referring still further to FIGS. 1 and 2, the system 10 also includes a compression paddle or plate 28 and a support structure 30 to which one or more of the radiation source 16, radiation detector 18, and/or compression plate 28 may be mounted to. In embodiments, the system 10 may further include a controller 32. The controller 32 may be a workstation having at least one processor/central processing unit/computer and a memory device/database that stores information and/or instructions for the operation of the system 10 that are employed by the controller 32, as shown in FIG. 1 or, in other embodiments, the controller 32 may be embedded/integrated into one or more of the various components of the system 10 disclosed above. In embodiments, the controller 32 may be in electrical communication with the radiation source 16, radiation detector 18, and/or the compression plate 28 via a cable 34. As will be appreciated, in embodiments, the connection 34 may be a wireless connection. In embodiments, the controller 32 may include a radiation shield 36 that protects an operator of the system 10 from the radiation rays 22 emitted by the radiation source 16. The controller 32 may further include a display 38, a keyboard 40, mouse 42, and/or other appropriate user input devices that facilitate control of the system 10 via a user interface 44.

As further shown in FIGS. 1 and 2, the radiation source 16, along with the radiation detector 18, forms part of an x-ray system which provides x-ray imagery for the purpose of imaging a body part of a patient, such as breast 52. As stated above, the radiation source 16 emits the radiation rays 22 such that the radiation rays 22 travel from the radiation source 16 to the radiation detector 18. While the radiation rays 22 are discussed herein as being x-rays, it is to be understood that the radiation source 16 may emit other types of electromagnetic rays which can be used to image a patient. The radiation source 16 may be mounted to the support structure 30 such that the radiation source can rotate around an axis 46 in relation to the radiation detector 18, although movement of the radiation source 16 in paths other than rotation about a fixed axis, such as during digital breast tomosynthesis (DBT), are also envisioned. In embodiments, the radiation detector 18 may be configured to rotate or translate within its housing, such as in the directions indicated by arrows 53 and 55.

In the illustrated exemplary embodiment of FIG. 1 the radiation source 16 and the detector 18 are mounted to a gantry 90 that is secured to the support structure 30. The support structure 30 houses a translation mechanism 92 that is operably connected to the gantry 90. The translation mechanism 92 is operable to move the gantry 90 vertically with respect to the support structure 30 in order to position the gantry 90 at the appropriate height to accommodate the dimensions of the patient on which the system 10 is being utilized. The translation mechanism 92 is also operable to rotate the gantry 90 relative to the support structure 30 about the horizontal axis 46 in order to position the gantry 90 rotationally with regard to the patient, as necessary.

The gantry 90 includes a generally C-shaped body 94 with the radiation source 16 at one end and the detector 18 at the opposite end. In this configuration, regardless of the vertical and/or rotational orientation of the gantry 90, such as to position the radiation source 16 and detector 18 relative to the patient breast 52 to obtain x-ray images at various orientations, such as for craniocaudal (CC) or mediolateral oblique (MLO) views, among others, the radiation source 16 is disposed in alignment with the detector 18. In this position, the detector 18 is capable of receiving the x-rays 22 emitted from the radiation source 16 that pass through the portion of the patient, i.e., patient breast 52, located between the radiation source 16 and the detector 18 in order to generate image data for transmission to the control system 32 of the mammography device/system 10 to create/reconstruct a 3D image dataset for viewing by a physician, such as by using DBT, among other known methods.

Additionally, in another embodiment the radiation source 16 can be attached to the gantry 90 to rotate and/or move independently of the gantry 90 and detector 18 in order to enable the radiation source 16 to take x-ray images of the patient breast at various angles relative to the detector 18, e.g., between +/−60°. The images obtained between these angles for the radiation source 16 can be used either for creation of stereoscopic images in a biopsy procedure using the system 10 or for DBT when operating the system 10 in an imaging mode.

As stated above, the radiation detector 18 receives the radiation rays 22 emitted by the radiation source 16. In embodiments, data regarding the radiation rays 22 received by the radiation detector 18 may be electrically communicated to the controller 32 from the radiation detector 18 via cable/electronic connection 34 such that the controller 32 generates one or more images which may be shown on the display 38 and stored in the memory device.

The compression plate 28 is operative, in response to instruction from the controller 32 or in response to instructions from controller(s) on or near the mammography system 10 or switch controllers 80, to move towards and away from the radiation detector 18 as indicated by arrows/compression axis 48 such that the compression plate 28 flattens and holds a body part, e.g., breast 52, in place against the surface 50 of the radiation detector 18. In this respect, the radiation detector 18 and the surface 50 thereof is referred to herein as a "support plate" that cooperates with the compression plate 28 to compress and clamp a breast of a patient therebetween.

In one exemplary embodiment, in order to maintain the position of the patient breast 52 stationary during the imaging and/or biopsy procedures, the compression plate 28 is attached to a plate or paddle support mechanism 45 located on and/or within the gantry 90 that positions the compression plate 28 directly over and in alignment with the detector 18/support plate and operably connected to the controller 32.

The plate support mechanism 45 is operable within the gantry 90 at any rotational or vertical position of the gantry 90 to move the plate 28 in a line either towards or away from the detector 18/support plate. The mechanism 45 can have any of a number of different configurations, but in one exemplary embodiment takes the form of a compression screw mechanism that is operable to move the plate 28 into engagement with the patient breast 52 to exert a predetermined pressure/compression on the breast 52 to retain the breast 52 in a stationary position between the plate 28 and the detector 18/support plate during imaging and/or biopsy procedures.

In operation, in accordance with an embodiment, the breast 52 of the patient may be placed onto the surface 50 of the radiation detector 18. The compression plate 28, under control of the plate support mechanism 45 by the controller 32, moves towards the detector 18 to compress the breast 52 against the surface 50 of the detector 18 such that the breast 52 is immobilized. Movement of the compression plate 28 towards the detector 18 to compress the breast 52 against the support plate/detector 18 defines a compression phase of the system 10. Once a target compression is achieved, movement of the compression plate 28 is halted and the compression plate 28 and the support plate 18 are held in fixed position to clamp the breast 52 therebetween (referred to herein as the clamping phase) so that imaging or procedures, e.g., a biopsy, may be commenced. During an imaging procedure, the radiation source 16 is selectively adjusted such that it is moved/rotated to a first scanning position and scans the breast 52. The radiation detector 18 receives the radiation rays 22 passing through the breast 52 and sends data to the controller 32 which then generates one or more x-ray images of the breast 52. Once imaging is complete, the controller 32 moves the compression plate 28 away from the support plate 18 to free the breast 52.

Referring still further to FIG. 1, in an embodiment, the system 10 may include one or more physiological monitoring or sensor devices 54, 56, 58, 60 communicatively coupled with the controller 32 for monitoring one or more physiological parameters of a patient (and for transmitting physiological parameter data to the controller 32). While FIG. 1 illustrates that the sensor devices 54, 56, 58 are connected to the controller 32, in some embodiments, one or more of the sensor devices may be communicatively coupled with the mammography apparatus, without departing from the broader aspects of the invention. The sensor devices may be selected to monitor and/or measure any physiological information of a patient desired, including, but not limited to, diastolic blood pressure, systolic blood pressure, body temperature, blood oxygen level, patient weight, skin conductance, pulse rate, etc. As illustrated in FIG. 1, one or more of the sensor devices, e.g., sensor device 60, may be physically integrated with the compression plate 28 and/or the detector/support plate 18. By incorporating the sensor devices into the support plate 18 or compression plate 28, physiological parameter data of the patient may be acquired and transmitted to the controller 32 without requiring any additional intervention by the system operator.

In an embodiment, the sensor device 60 may be a force sensor for measuring the amount of pressure or compressive force applied to the breast 52. Additional sensors for measuring physiological parameters may be configured to either directly measure or allow the calculation of variables such as force, pressure, temperature, rigidity, elasticity, breast size and/or volume, and/or tissue density and could be embedded in compression plate 28 or support plate 18 or attached as part of mammography system 10.

The various sensor devices 54, 56, 58, 60 may be configured to acquire physiological parameter data and/or other sensor data from a patient during system operation. More specifically, physiological parameter data may be acquired continuously or at predetermined time intervals before breast compression and imaging, during the compression phase of the system and/or during the clamping phase of the system. In an embodiment, the physiological parameter data may be acquired continuously or at predetermined time intervals during at least the compression phase. In other embodiments, the physiological parameter data may be acquired continuously or at predetermined time intervals during at least the compression phase and the clamping phase.

Referring once again to FIG. 1, in an embodiment, operation of the system 10 during the compression phase and the clamping phase may be controlled by the patient using switch controls 80, e.g., footswitch controls, such as disclosed in U.S. Pat. No. 10,004,470, which is hereby incorporated by reference herein in its entirety. Switch controls 80 are typically connected via a cable/wire 82 to mammography imaging system 10. The controls are also often mirrored on the opposite side of mammography imaging system 10 (not shown). Other controls (not shown) may be present on particular accessories placed either in the paddle/breast support area. In an embodiment, rather than being footswitch controls, the switch controls may be a handheld control unit 84 with a wired, wireless, Bluetooth or other connection with the system 10. In an embodiment, the patient may control the rate of compression and/or pressure or force applied during the compression phase and/or clamping phase using the switch controls. A feedback device, e.g. controller 32, may be configured to give feedback information about the image to obtain and may designed such that the feedback information is operatively perceivable by the patient (e.g., through an audible or visual indication). The feedback device, e.g., controller 32, may be configured to provide feedback information to the patient regarding the rate of compression (greater or lower rate of compression) and/or amount of pressure (higher or lower) required to produce an optimal image, in dependence upon the information received from the various sensor devices 54, 56, 58, 60. In this respect, the feedback device informs the patient when compression rate and/or pressure applied is sufficient to obtain a quality image, as determined from a blood pressure or other measurement taken from the patient through sensing devices 54, 56, 58, or 60, before or during the compression and/or clamping phase.

Figure 3:
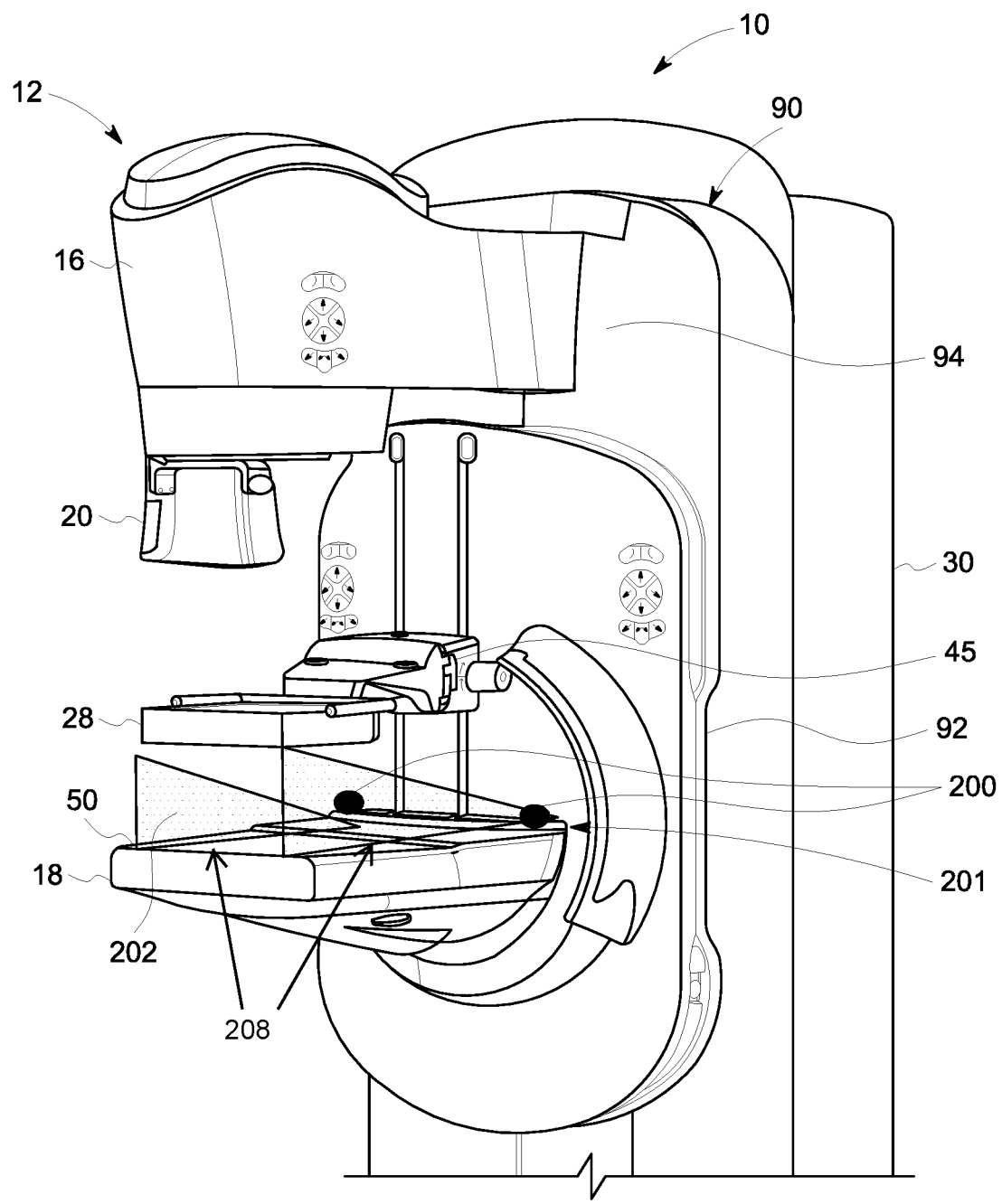
FIG. 3 is a perspective view of the mammography system of FIG. 1 including a pair of sensing devices forming a distance and location system in accordance with an embodiment of the disclosure.

Referring now to FIG. 3, the imaging system 10 further includes one or more of additional sensing devices 200 disposed in one or more positions on the gantry 90 to form a distance and location sensing system 201. The sensing device(s) 200 is capable of emitting one or more waves or beams 202 of sound or radiation that strike an object 204 disposed in the path of the wave(s)/beam(s) 202 emitted from the sensing device 200. Upon striking the object 204, the wave(s)/beam(s) 202 are reflected back to the sensing device 200. The reflected wave(s)/beam(s) 202 provide information to the sensing device 200 regarding the presence, shape, and location of any object 204 in the path of the wave(s)/beam(s) 202 as well as the distance of the object 204 from the sensing device 200. This information is provided by the time elapsed between the emission of the wave(s)/beam(s) 202 from the sensing device 200 and the return of the beam(s) 202 to the sensing device 200 and is analyzed by sensing device 202 and/or the controller 32, which is operably connected to the sensing devices 200, in order to make these determinations. Suitable sensing devices 200 that emit wave(s)/beam(s) 202 to obtain this type of information include ultrasound (US) sensing devices, microelectromechanical systems (MEMS) radar sensing devices, and time of flight (ToF) sensing devices, among others. In one exemplary embodiment, the sensing device 200 emits wave(s)/beam(s) to be reflected of an object 204 that do not interfere with the operation of the imaging system 10 and that do not create a harmful condition with regard to the object 204 that is contacted by and that reflects the wave(s)/beam(s) 202.

Figure 4:
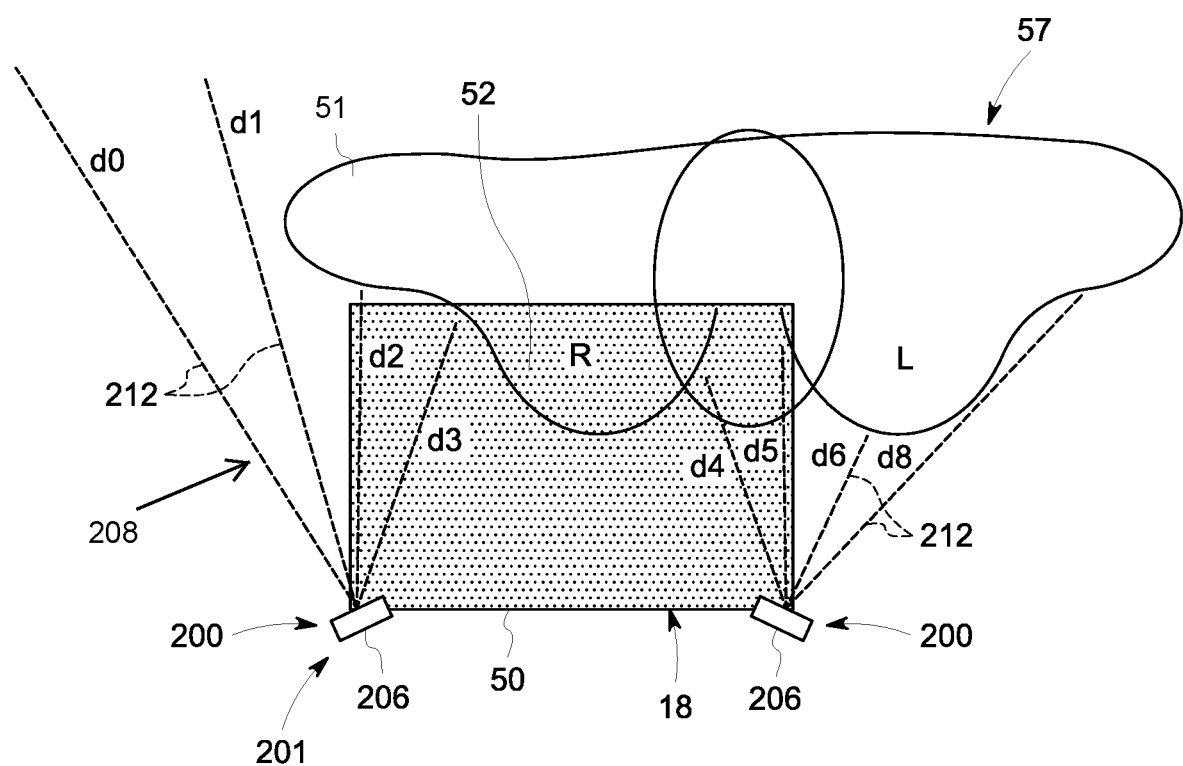
FIG. 4 is a schematic view of the distance and location system of FIG. 3 performing a laterality determination on the breast of a patient.
Figure 5:
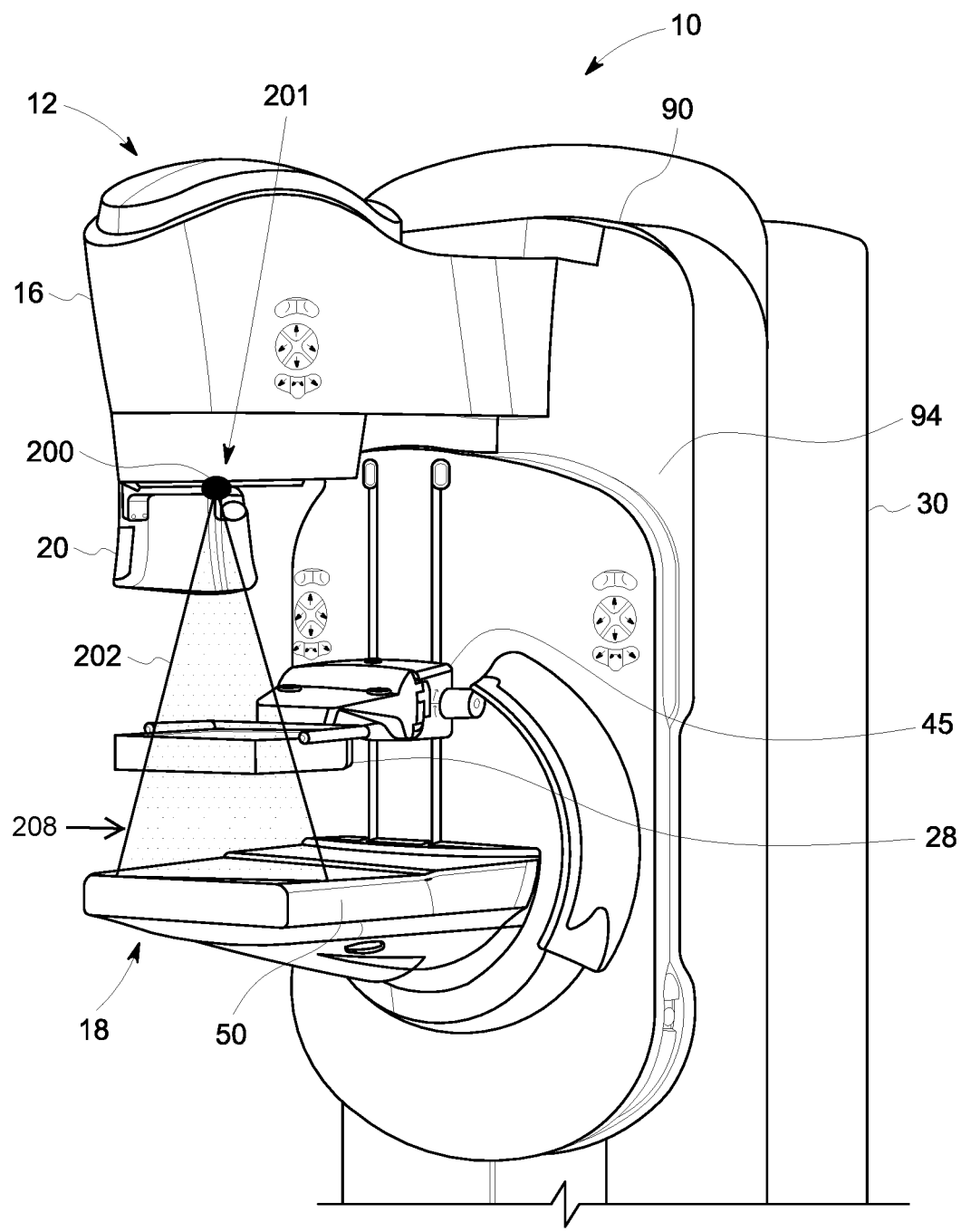
FIG. 5 is a perspective view of the mammography system of FIG. 1 including a sensing device forming a distance and location system in accordance with another embodiment of the disclosure.
Figure 6:
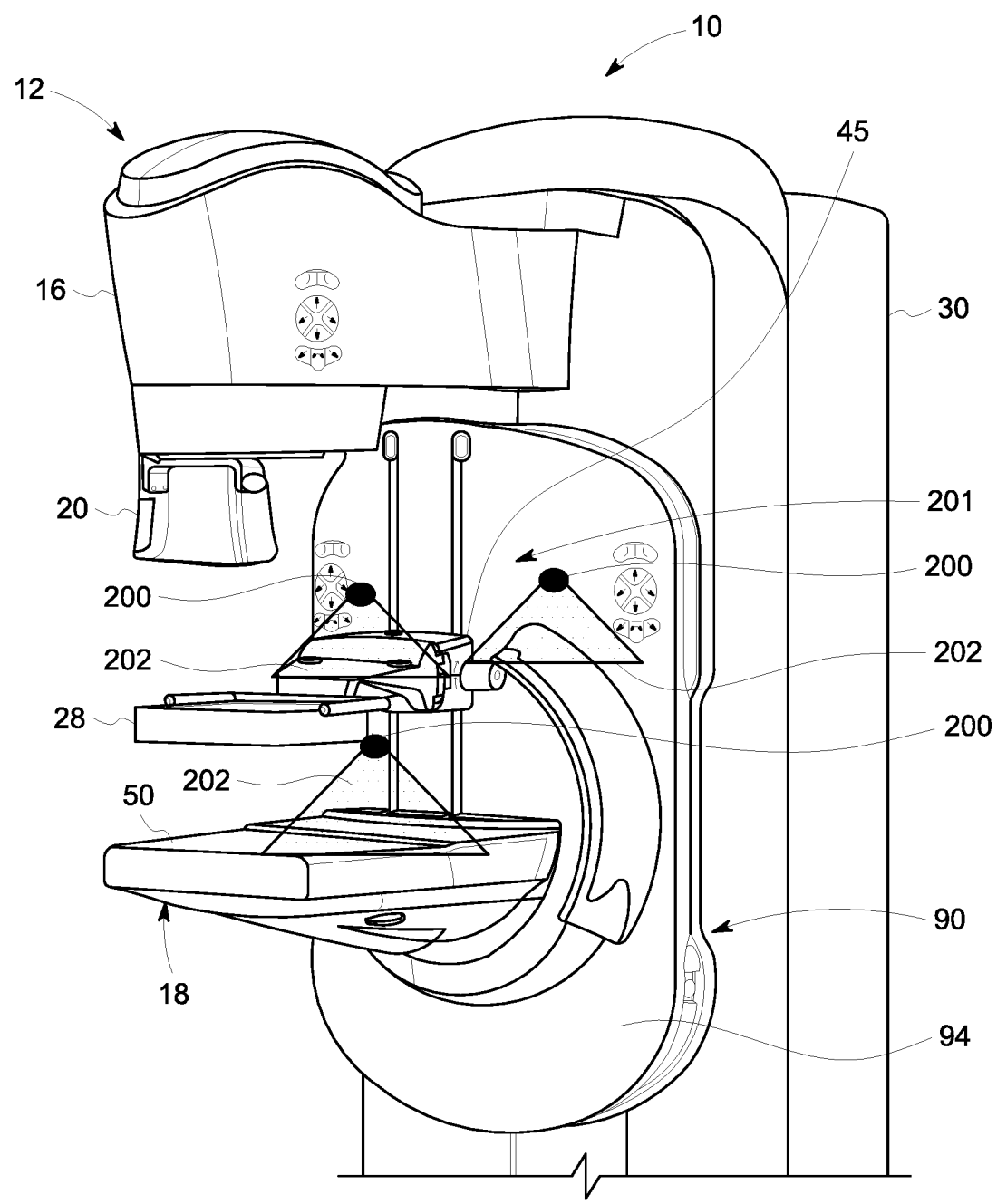
FIG. 6 is a perspective view of the mammography system of FIG. 1 including a pair of sensing devices forming a distance and location system in accordance with another embodiment of the disclosure.

In the illustrated exemplary embodiment of FIGS. 3-5, the imaging system 10 includes at least one (FIG. 5) and in other embodiments a pair (FIGS. 3 and 4) of sensing devices 200 disposed on the detector 18/support plate and oriented to emit the wave(s)/beam(s) 202 towards the object 204. In FIGS. 4 and 5, the object 204 is represented as a breast 52 disposed on the detector 18/support plate to be imaged by the system 10. The sensing devices 202 can also be positioned in different locations or combinations of locations to accommodate for the positions of the sensing devices 200 required to emit wave(s)/beam(s) 202 for determination of the locations of various structures of the imaging system 10 and/or the object 52/204. In particular, as shown in FIGS. 5 and 6, the sensing device(s) 202 can be positioned on or adjacent the radiation source 16 (as the compression plate 28 is transparent to the waves or radiation emitted by the sensing device(s) 200), on the compression plate 28, and/or at various locations on the gantry 90, either as alternatives or in addition to the placement on the detector 18, in order to provide position information from different perspectives on the locations of various components of the imaging system 10, as well as the patient 57.

With particular reference again to FIGS. 3 and 4, the disposition of the sensing device 200 on the surface 50 of the detector 18 enables the sensing device 200 to emit the wave(s)/beam(s) 202 outwardly towards a breast 52 positioned on the surface 50. In one particular exemplary embodiment, the sensing device(s) 200 can take the form of a ToF sensor 206, such as the ST Microelectronics FlightSense™ ToF sensor (https://www.st.com/en/imaging-and-photonics-solutions/time-of-flight-sensors.html). The ToF sensor 206 emits photons into a coverage zone 208 containing a number of individual sectors 212 forming the coverage zone 208. The photons are reflected off of a target, such as the breast 52, and return to the ToF sensor 206 for a determination of the distance to the breast 52 from the sensor 206 resulting from the time elapsed from the emission of the photon from the sensor 206 to the sensing of the reflected photon by the sensor 206. The sensor 206 enables multiple photons to be emitted into or across the coverage zone 208 (FIGS. 3-5) in the area targeted by the one or more sensors 206. In one exemplary embodiment, the zone 208 can encompass an 8×8 matrix or grid 210 of individual sectors 212, with each sector 212 within the grid 210 capable of returning a separate location and/or distance determination for any object 52/204 reflecting the photon directed into the particular sector 212, thereby providing a distance map 214 of the object(s) 52/204 detected as being present within the grid 210.

As illustrated in FIG. 4, in order to determine the laterality of the breast 52 disposed on the surface 50 of the detector 18, each of the pair of ToF sensors 206 can emit multiple photons/beams 202 into different sectors 212 d1-d8 in front of the ToF sensors 206. As the patient 57 has only a single breast 52 disposed on the surface 50, the other breast 52 will be disposed to one side of the surface 50. Therefore, the determination of which breast 52 is disposed on the surface 52 can be made through the reflection of the emitted photons/beams 202 off of the breast 52 and the remainder of the patient 53 positioned facing the ToF sensors 206. As shown in the example of FIG. 4, with the right breast 52 positioned on the surface 52, the left side of the patient 57 is disposed in front of the ToF sensor 206 on the right side of the surface 50. Thus, the photons/beams 202 emitted from the ToF sensor 206 covering sectors d5-d8 of the distance map 214 will contact the left side of the patient 57 and be reflected back to the ToF sensor 206. Similarly, the photons/beams 202 emitted from the ToF sensor 206 covering sectors d1-d4 of the distance map 214 will also strike the patient 57 and be reflected back to the ToF sensor 206. However, as the position of the patient 57 does not extend into sectors d1 or d2, the photons/beams 202 directed by the ToF sensor 206 into sectors d1 and d2 will miss the patient 57 and instead will strike and be reflected off of a surface that is an increased distance behind the patient 57. This return delay/increase in the return time for the photons/beams 202 in sectors d1 and d2 can be utilized by the controller 32 to determine that the patient is positioned only within sectors d3-d8 of the resulting distance map 214. As such, with the known position of a breast 52 on the surface 50, and the location of the patient 57 determined within sectors d3-d8, the controller 32 is able to ascertain the laterality of the breast 52 on the surface 50, i.e., that the breast 52 is the right breast 52. Conversely, if the ToF sensors 206 determine that the patient 53 is disposed only in sectors d1-d6, the controller 32 can determine the laterality of the breast 52 on the surface 50 as being the left breast 52.

The ability of the ToF sensors 206 to detect the presence of the body of the patient 57 for determining the laterality of the breast 52 being imaged also enables the ToF sensors 206 to detect parts of the patient 57 other than the breast 52 that may be within the imaging area of the imaging system 10. For example, if an arm 51 of the patient 57 is located too close to the detector 18 and/or is within the FOV of the radiation source 16, the ToF sensors 206 can detect the presence and location of the arm 51 using the photos emitted from the ToF sensors 206 that are reflected back to the ToF sensors 206 from sectors outside of the area of the detector 18/support plate. In particular, as shown in the exemplary embodiment of FIG. 4, the right arm 51 of the patient 57 is located immediately adjacent the detector 18. As such, the photons emitted from the ToF sensor 206 into sectors d1 and/or d2 strike and are reflected by the arm 51 back to the ToF sensor 206. The time taken for the photon(s) to travel to and from the arm 51 is greater than the photos striking the breast 52 on the detector 18, but shorter than those traveling to and from a more remote surface, e.g., a wall behind the patient 57. As a result, the ToF sensors 206 and/or controller 32 can use this information to determine the presence of the arm 51, and the position of the arm 51 relative to the detector 18. With this information, the controller 32 can alert the technician regarding the position of the arm 51Ip, so that the patient 57 can be move the arm 51 out of the FOV of the imaging device 10. The positions of the breast 52 and any other portions of the body of the patient 57, e.g., the arm 51, can additionally be detected through the use of one or more sensing device(s) 200 and/or ToF sensors 206 disposed at various positions and/or angles with regard to the detector 18, such as on the support plate 50 and on one or more of the radiation source 16 (FIG. 5) or the paddle/plate 28 (FIG. 6), among other suitable locations.

In addition to the laterality determination for the breast 52, as best shown in FIG. 5, the ToF sensors 206 are positioned in known locations with regard to the surface 50 of the detector 18. Thus, the ToF sensors 206 can emit photons/beams 202 across the breast 52 positioned on the surface 50 to determine a distance map 214 illustrating the shape of the breast 52 on the surface 50, including the position of the nipple 216 which can be utilized to identify the center of the breast 52. With the known position of the surface 50 relative to the sectors d1-d8 scanned by the ToF sensors 206 based on the known relationship between the surface 50 and the positions of the ToF sensors 206, the sensed location of the nipple 216 within the sectors d1-d8 of the distance map 214 can be correlated to a position on the surface 50 by the ToF sensors 206 and/or the controller 32. In this manner, the position of the nipple 216, or any other indication of a center of the breast 52, can be compared with the position of the surface 50 to determine if the breast 52 is properly disposed on the surface 50 prior to compression and/or an imaging procedure. If the controller 32 and/or ToF sensors 206 determine the breast 52 is not properly positioned on the surface 50, and indication can be provided to the technician not only of the improper positioning, but of the forward/back and left/right correction(s) necessary to achieve the proper position for the breast 52 on the surface 50.

Figure 7:
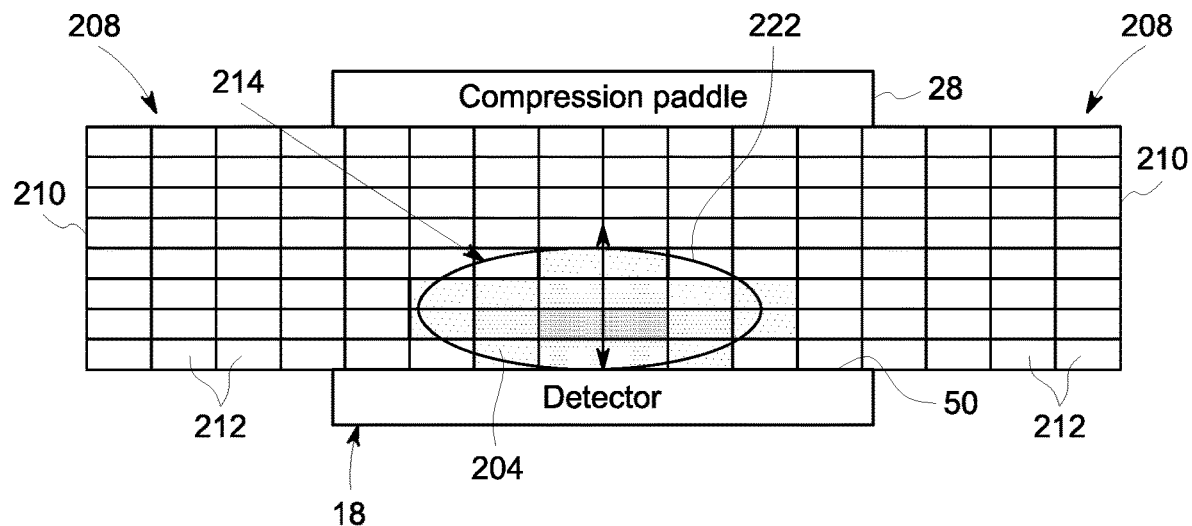
FIG. 7 is schematic view of a breast shape determination performed by the distance and location system of FIG. 3 in accordance with another embodiment of the disclosure.

The information obtained by the various sensing device(s) 200, e.g., ToF sensor(s) 206, can additionally be utilized to provide a representation of the shape of the breast 52 disposed on the surface 50 of the detector 18 prior to compression of the breast 52. Referring now to exemplary embodiment illustrated in FIG. 7, the sensing device(s) 202 take the form of a pair of ToF sensor(s) 206 disposed on or adjacent the surface 50 of the detector 18, similar to the configuration of the imaging system of FIG. 3. The ToF sensors 206 each emit photons into adjacent zones 208 each formed of an 8×8 grid 210 of individual sectors 212. The zones 208 cover the exemplary emission area 220 between the compression plate 28 and the detector 18 in order to determine the presence and shape of an object, e.g., a breast 52, disposed on the surface 50 of the detector 18. The travel time of the photons emitted by the ToF sensors 206 into each sector 212 provides the ToF sensors 206 and/or the controller 32 operably connected to the sensors with sufficient information to determine the position of the breast 52 on the surface 50. Further, by employing a suitable matrix segmentation of the distance information provided for each sector 212, the sensors 206 and/or controller 32 can additionally determine the shape of the breast 52 as positioned on the detector 18. As shown in FIG. 7 the matrix segmentation over the individual sectors 212 forming the matrix or grid 210 provides a close estimation for the shape 222 of the breast 52 using information obtained regarding those sectors 212 indicating the presence of the breast 52. In FIG. 7, based on the horizontal orientation of the ToF sensors 206 with regard to the breast 52. The shape 222 determined by the ToF sensors 206 is a front elevational shape of the breast 52. However, with sensing devices 200/ToF sensors 206 disposed at alternative or additional locations on the imaging device/system 10 (see FIGS. 5-6), additional shapes 222 of the breast 52 can be generated from different perspectives, e.g., a top plan shape, right and/or left side elevation shape, etc. in manner similar to that previously described. The additional shapes 222 provided by sensing devices 200/ToF sensors 206 at other locations can be combined with the shape 22 in FIG. 7 to derive a 3D representation of the shape of the breast 52.

With this shape information, whether provided by sensing devices 200/ToF sensors 206 enables the controller 32 to match the compression plate 28 to the detected shape 22 of the breast 52. In one manner of doing so, the configuration of the compression plate 28 is input into the imaging system 10, either manually by the technician using one or more of the input devices connected to the imaging system/devoice 10, i.e., the keyboard 40 and/or the mouse 42, or automatically by scanning a suitable identifier (not shown) on the plate 28 containing information about the configuration of the plate 28. Alternatively, the configuration of the plate 28 can be obtained through the use of the sensing device 200/ToF sensors 206, which can scan the plate 28 when disposed within the zones 208 covered by the sensing devices 200/ToF sensors 206, with the distance information obtained by the sensing devices 200/ToF sensors 206 transformed by the controller 32 into a determination of the configuration of the plate 28.

With the information concerning the configuration of the plate 28, the controller 32 can compare the shape 222 of the breast 52 ascertained by the sensing devices 200/ToF sensors 206 to the shape and/or configuration of the plate 28. Should there be a significant difference between the plate configuration and the breast shape 222, the controller 32 can alert the technician of the difference and/or provide information to the technician regarding the plate 28 with the proper shape or configuration most closely matching the shape 22 for the breast 52 to be employed for the imaging and/or biopsy procedure to be performed. In an exemplary embodiment, the information concerning the proper plate 28 to be employed for the imaging procedure can be provided from a database (not shown) of available plates 28 and the specifications/configurations for each plate 28, that can be accessed by the controller 32 for determining a plate 28 having the desired configuration to complement the detected parameters for the breast 52.

According to another exemplary embodiment of the disclosure, referring now to FIGS. 7-10, the location information provided by the sensing device(s) 200/ToF sensor(s) 206 can be employed by the controller 32 to control the movement of the compression plate 28. As shown in FIG. 7, when the breast 52 is initially positioned on the surface 50, the plate 28 is spaced from the surface 50, but is at least partially disposed within the area 220 encompassed within the coverage zone(s) 208 of the sensor(s) 206. A such, the sensor(s) 206 can determine the distance between the breast 52 and the compression plate 28, in addition to the location and shape of the breast 52 on the surface 50.

Figure 8:
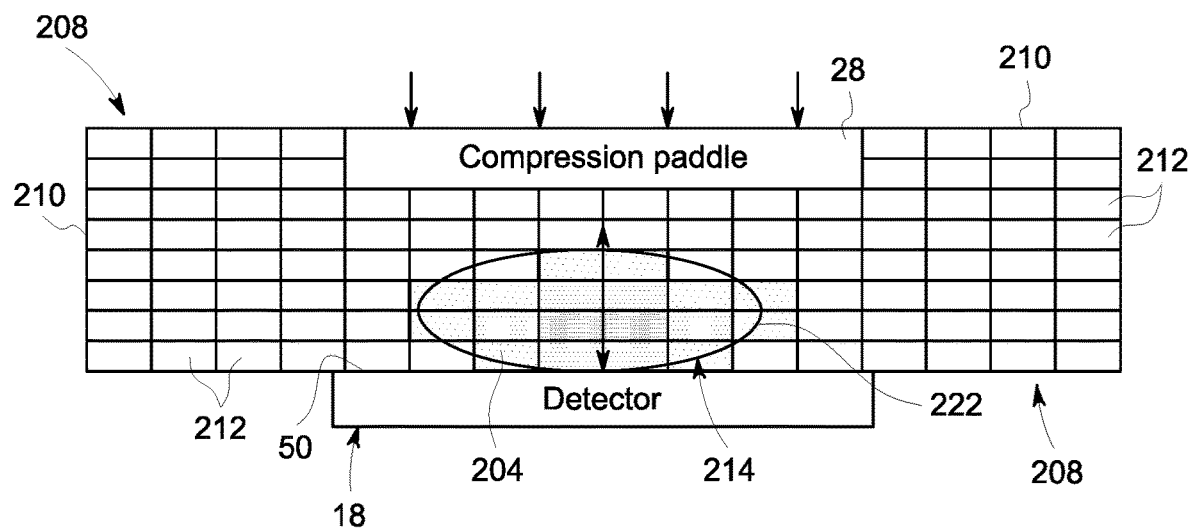
FIG. 8 is schematic view of the determination of locations of a compression plate and breast performed by the distance and location system of FIG. 3 in accordance with an embodiment of the disclosure.
Figure 9:
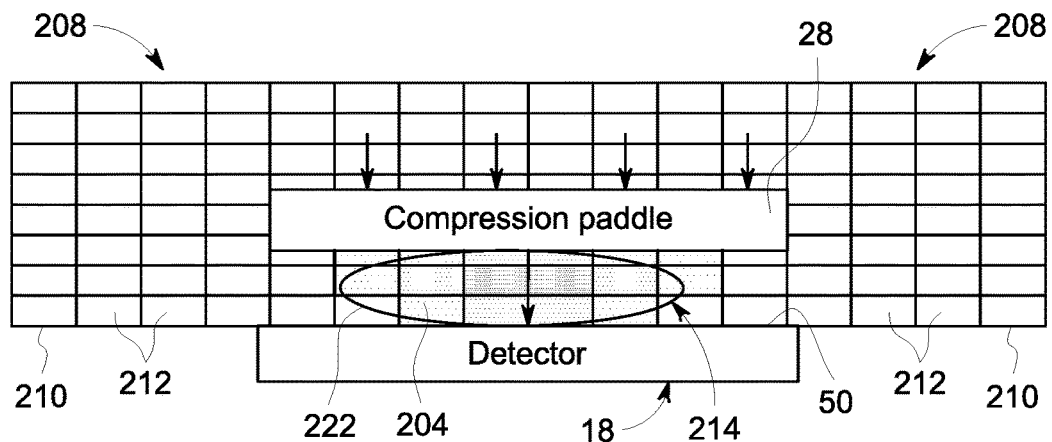
FIG. 9 is schematic view of the determination of locations of a moving compression plate and breast after initial contact with the breast performed by the distance and location system of FIG. 3 in accordance with an embodiment of the disclosure.
Figure 10:
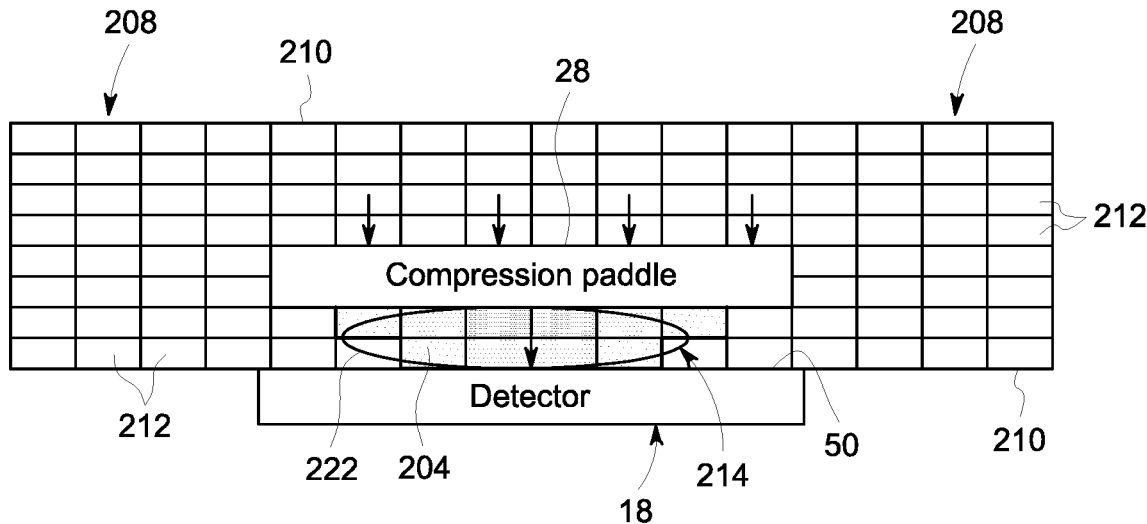
FIG. 10 is schematic view of the determination of locations of the compression plate and breast at final compression of the breast performed by the distance and location system of FIG. 3 in accordance with an embodiment of the disclosure.

Looking now at FIGS. 8-10, as the compression plate 28 is lowered towards to the breast 52, the position of the compression plate 28 can be continually determined by the operation of the sensing device(s) 200/ToF sensor(s) 206, which are capable of being operated while the controller 32 moves the compression plate 28 prior to the imaging procedure. In FIG. 8, while the compression plate 28 is moved downwardly towards the breast 52, the position of the compression plate 28, and thus the distance between the plate 28 and the breast 52 is continuously determined, thereby providing the controller 32 with real time information regarding the distance between the plate 28 and the breast 52 as the plate 28 moves toward the breast 52. In this manner the controller 32 can gauge and/or monitor the rate of change of the distance between the compression plate 28 and the breast 52.

Looking now at FIG. 9, as the compression plate 28 begins to contact the breast 52, i.e., when the detected distance between the plate 28 and the breast is 0, or just prior to the contact of the compression plate 28 with the breast 52, the controller 32 can slow down the rate of movement of the plate 28 towards the breast 52. This control of the speed of movement of the compression plate 28 can be done in conjunction with the manual operation of the plate support mechanism 45, where the distance data from the sensing device(s) 200/ToF sensor(s) 206 supplied to the controller 32 enables the controller 32 to provide an automatic braking function with regard to the movement of the compression plate 28. Alternatively, the control of the speed of movement of the plate 28 via the plate support mechanism 45 can be performed independently by the controller 32 using the location/distance data provided to the controller 32 by the sensing device(s) 200/ToF sensor(s) 206.

Looking now at FIG. 10, as the plate 28 compresses the breast 52 after initially contacting the breast 52, the controller 32 can further control, i.e., slow the movement of the plate 28, and ultimately stop all operation of the plate support mechanism 45 and corresponding movement of the plate 28 upon reaching the desired compression for the breast 52 in view of the distance or position information of the plate 28 and breast 52 relative to one another and to the detector 18 as provided to the controller 32 by the sensing device(s) 200/ToF sensor(s) 206. Again, similarly to the speed control/slowing of the operation of the plate support mechanism 45 and movement of the plate 28 by the controller 32 prior to contact of the plate 28 with the breast 52, the movement of the plate 28 to compress the breast 52 can be performed automatically by the controller 32 or in conjunction with the manual operation of the plate support mechanism 45.

In addition, similar to the determination of the 3D representation of the breast 52 prior to movement of the compression plate 28 by utilizing distance and/or location data obtained from sensing device(s) 200/sensor(s) 206 located on or adjacent the surface 50, as well as on the plate 28 and/or on the gantry 90 in suitable locations, the distance data from each of the sensing device(s) 200/ToF sensor(s) 206 at different locations on the imaging device 10 can be employed to determine a change in the shape 222 of the breast 52 as the breast 52 is compressed by the plate 28. This determination enables the controller 32 to calculate the changing thickness of the breast 52 as it is being compressed by the plate 28, thereby allowing the controller 32 to operate the plate support mechanism 45 to move the plate 28 to a position where the breast 52 is compressed to achieve the optimal thickness for obtaining images of the breast 52. Further, the compression of the breast 52 to the desired thickness can be performed with the controller 32 operating the plate support mechanism 45 in the aforementioned manner to gradually or slowly compress the breast 52 to minimize discomfort to the patient 57 during the compression steps. In connection with the above, it is generally understood that better image quality can be achieved by flattening the breast to a greater degree, by applying a greater compressive force. Increased compressive force, however, is known to cause pain and discomfort for patients. By monitoring the shape 222 of the breast 52 during the compression and clamping phases, the system 10 is able to optimize the compressive force applied and/or the rate of compression to minimize patient discomfort while also ensuring that a minimum level of compression is achieved to ensure that quality images can be obtained. In embodiments, the feedback from the various sensing devices allows for automated, real-time changes in compression based on factors that ensure optimal image quality while at the same time attempting to minimize discomfort experienced during the procedure.

Figure 11:
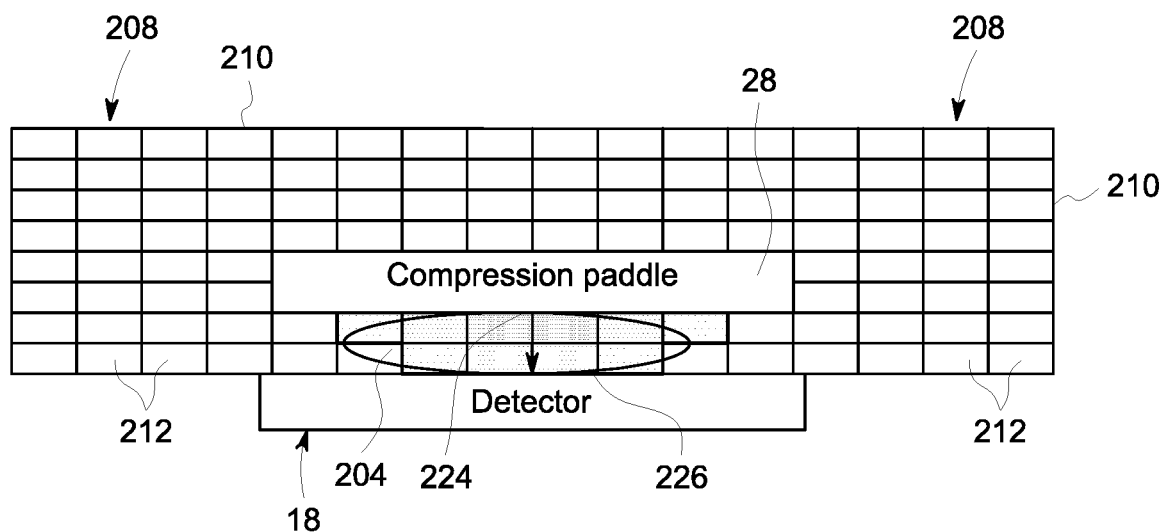
FIG. 11 is schematic view of the determination of an estimated pressure exerted on the breast at final compression of the breast performed by the distance and location system of FIG. 3 in accordance with an embodiment of the disclosure.

In conjunction with the distance information concerning the changing positions of the compression plate 28 and breast relative to one another and to the detector 18/surface 50, the information provided to the controller 32 by the sensing device(s) 200/ToF sensor(s) 206 as the plate 28 compresses the breast 52 allows for determinations of the pressure being exerted on the breast 52 during compression. In particular, referring now to FIG. 11, the information provided by the sensing device(s) 200/ToF sensor(s) 206 concerning the shape 222 of the breast 52, both prior to and during compression, enables the controller 32 to determine a contact area 224 of the breast 52 with the compression plate 28, and a contact area 226 of the breast 52 with the surface 50 of the detector 18. OIN FIG. 7, prior to any contact of the compression plate 28 with the breast 52, the breast 52 only has a contact area 226 on the surface 50. Upon initial contact of the plate 28 with the breast 52 (FIG. 8), the breast 52 also creates a contact area 224 with the plate 28. Upon further movement of the plate 28 towards the surface 50 to compress the breast 52 between the plate 28 and the surface 50, the contact areas 224, 226 become larger, as shown in FIGS. 9 and 10.

As the contact areas 224, 226 are enlarged by the movement of the compression plate 28 towards the detector 18/surface 50, the size of the areas 224, 226 can be determined by the sensing device(s) 200/ToF sensor(s) 206. In particular, in conjunction with the determination of the shape 222 of the breast 52, the controller 32 can calculate the contact areas 224, 226 disposed against the plate 28 and the surface 50. Using these calculated contact areas 224, 226, the controller 32 can further compute a pressure that is being exerted on the breast 52 by the compression plate 28 and the surface 50. The determination of the size of the contact areas 224, 226 can be performed continuously, i.e., in real-time, throughout the compression of the breast 52 in order to allow the controller 32 to continuously monitor the pressure being exerted on the breast 52. This pressure measurement can also be employed by the controller 32 to provide another manner of controlling the operation of the plate support mechanism 45 to position the plate 28 against the breast 52, such as by moving the plate 28 to compress the breast 52 without exceeding a maximum threshold value or targeted compression or pressure value for the pressure to be exerted on the breast 52.

As the controller 32 can be configured to determine the pressure on the breast 52 during compression utilizing only the distance information provided by the sensing device(s) 200/ToF sensor(s) 206, the need for a separate force or pressure sensor 60 on the surface 50 is negated. However, in certain embodiments where the force sensor 60 is already part of an imaging system/device 10 being modified to include the sensing device(s) 200/ToF sensor(s) 206 and accompanying instructions to be stored in memory on the imaging system 10 for the operation of the controller 32 using the distance information from the sensing device(s) 200/ToF sensor(s) 206, the force sensor 60 can be included as a separate manner for the determination of the pressure exerted on the breast 52.

In operation, regarding the various embodiments discussed previously concerning the construction and operation of the distance and location sensing system 201, the controller 32 is configured to control movement of the compression plate 28 toward the support plate 18 to flatten the breast 52 during the compression phase, and to clamp the breast 52 during the clamping phase, as discussed above. The controller 32 is also configured to control movement of the compression plate 28 to adjust at least one of a rate of compression and/or a pressure or compressive force applied to the breast 52 in response to the physiological parameter data acquired from the patient. For example, in an embodiment, the controller 32 is configured to vary the at least one of the rate of compression and/or the pressure applied to the breast 52 during the compression phase and/or clamping phase based on measurements provided to the controller 32 by the distance or location sensing system 201 regarding of at least one of the shape 222 of the breast 52, the thickness of the breast 52, and/or a computes pressure exerted on the breast 52 taken in a continuous or real-time manner during the compression phase and/or the clamping phase.

In particular, in embodiments where certain distance measurement(s) are obtained via the distance and location sensing system 201 continuously during the compression phase and the clamping phase, the controller 32 may be configured to vary at least one of the rate of compression and/or the pressure applied in real-time, as practicable, as any one or more of these measured distances and associated parameters change. As used herein, "real-time" refers to a level of responsiveness that a user senses as sufficiently immediate, or that enables the controller (or other processor) to keep up with an external process, e.g., compression, pressure, etc. As used herein, "rate of compression" refers to the change in compressive force applied to the breast in relation to elapsed time. In an embodiment, at least one of the rate of compression and/or the pressure applied may be varied in real-time during the compression phase, and a target pressure has been reached for optimal image acquisition, the clamping phase may be initiated and the plates held in static position during the scan (2D, DBT, multi-energy, etc.). This ensures that the object being imaged remains in the same position during the scan.

Figure 12:
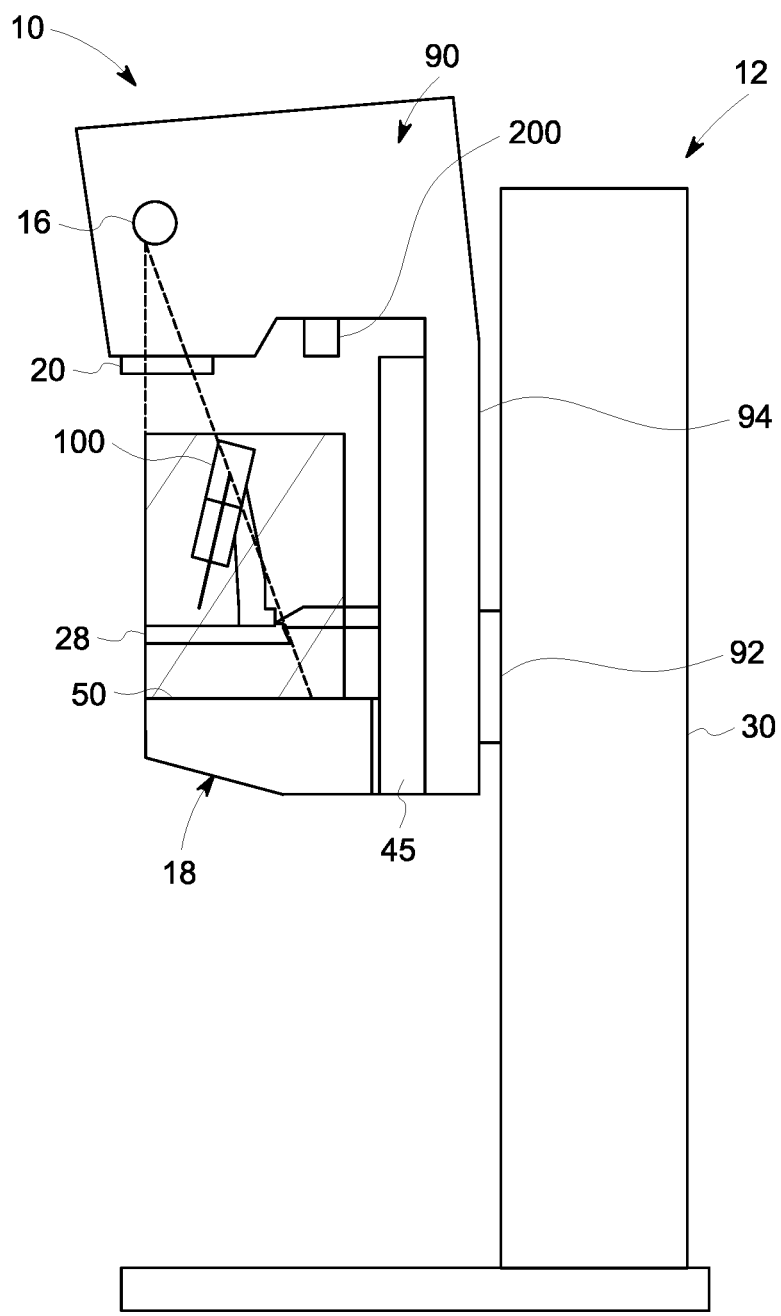
FIG. 12 is an isometric view of another embodiment of the mammography system of FIG. 1 including a biopsy device, in accordance with an embodiment of the invention.

In another exemplary embodiment, as shown in FIGS. 12-15 the system 10 may further, or alternatively, include a biopsy system 100, which may be selectively removable from the imaging system 10. In such an embodiment, the radiation source 16, along with the radiation detector 18, forms part of an x-ray system which provides x-ray imagery for the purpose of guiding the biopsy tool 100 to a suspect site within a body part of a patient. As shown in FIG. 12, in embodiments, the biopsy system 100, may be disposed on the support structure 30 such that it also rotates about the axis 46, in a manner similar to the radiation source 16, and/or moves in a vertical and/or horizontal direction, in a manner similar to the compression plate 28.

Referring again to FIGS. 12 and 13 the biopsy system 100 includes a biopsy device or gun 102 that is moveably mounted to the gantry 90, optionally in a removable manner In the illustrated exemplary embodiment, the biopsy device 102 includes a movable biopsy needle 104 having a tip 106, and is mounted generally opposite the needle 104 to the gantry 90 via a robotic arm 108 that extends between the biopsy device 102 and the compression paddle 28. The robotic arm 108 can include a number of different and independently articulatable component sections 110 connected to various motive mechanisms/motors 112 that provide a number of different degrees of movement to the robotic arm 108 and enable the robotic arm 108 to position the biopsy device 102 at the desired orientation and spacing relative to the patient breast 52 positioned between the compression paddle 28 and the detector 18. The needle 104 is mounted to an end effector 114 disposed in the section 110 opposite the gantry 90, where the end effector 114 can be operated to move or fire the needle 104 into the patient breast 52 when performing a biopsy procedure. In one exemplary embodiment, in addition to the movement afforded by the robotic arm 108, the biopsy device 102 can rotate+/−90° around an axis extending through the patient breast 52 and parallel to the axis of rotation for the sensor table/detector 18.

Opposite the needle 104 and end effector 114 of the biopsy device 102, the robotic arm 108 is operably mounted to gantry 90 to enable the robotic arm 108 to be supported by the gantry 90. Further, the robotic arm 108 includes operating connections through the gantry 90 between the motive mechanisms, e.g., servomotors (not shown) disposed on and/or within the various component sections 100 of the robotic arm 108 and the controller 32 to enable control of these mechanisms to position the biopsy device 102 where desired. While the robotic arm 108 can be mounted to the gantry 90 in any suitable position to place the end effector 114 and needle 104 in close proximity to the patient breast 52, such as on the detector 18, as in the illustrated exemplary embodiment of FIG. 12, or as in the illustrated exemplary embodiment of FIG. 13 the robotic arm 108 is secured to the compression plate 28. In this position, the robotic arm 108, and biopsy device 102 disposed thereon, can be moved along with the compression plate 28 by the paddle support mechanism 45.

Figure 13:
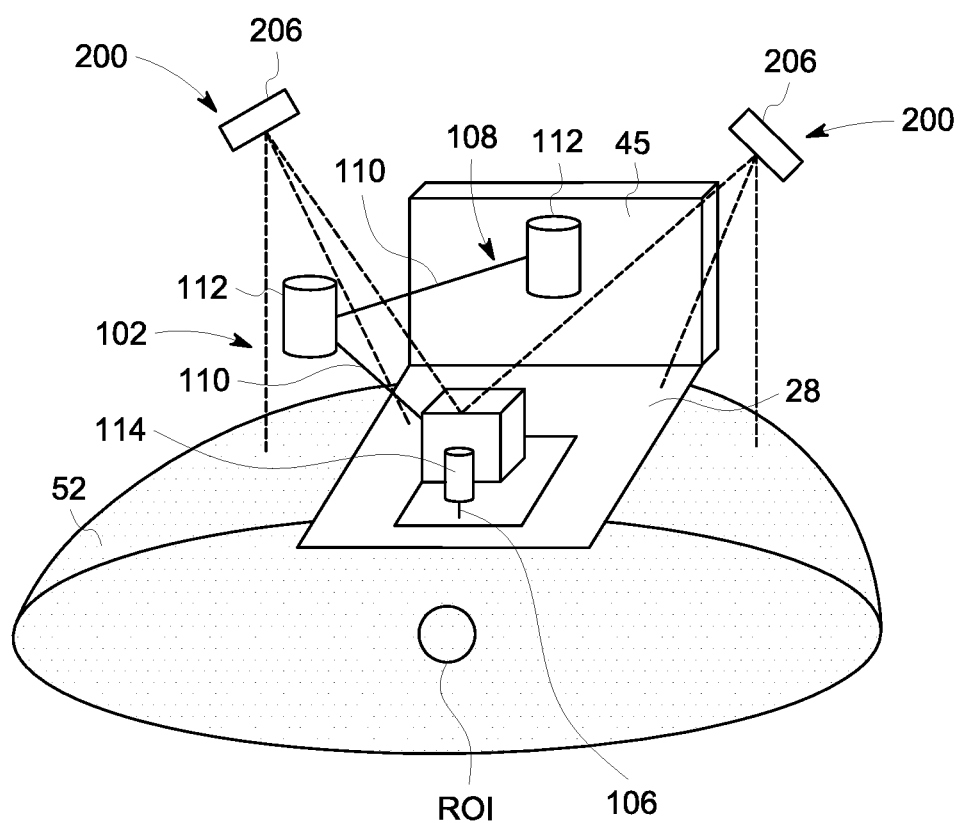
FIG. 13 is an isometric view of the mammography system of FIG. 12 performing a biopsy procedure, in accordance with an embodiment of the invention.

In the aforementioned embodiments of FIGS. 12 and 13, similarly to the operation of the distance and location sensing system 201 to obtain distance data from the sensing device(s) 200/ToF sensor(s) 206 to determine the location and shape of the compression plate 28 and the breast 52, as well as the changes in shape of the breast 52 when compressed between the plate 28 and the detector 18, in order to control the operation of the support plate mechanism 45 in moving the compression plate 28 to compress the breast 52, the distance data from the sensing device(s) 200/ToF sensor(s) 206 can also be employed to determine the location of the biopsy device 102 during the performance of a biopsy procedure on the system 10.

More specifically, the sensing device(s) 200/ToF sensor(s) 206 can be operated to additionally determine the location of the biopsy device 102 relative to the detector 18, which is fixed at least with respect to the connection point of the robotic arm 108 of the biopsy device 102 to the gantry 90, and the breast 52. In operation, the sensing device(s) 200/ToF sensors(s) 206 receive waves, radiation, or photons reflected off of the various components of the biopsy device 102 disposed within the zone(s) 208 covered by the sensing device(s) 200/ToF sensors(s) 206, such that the controller 32 can utilize the distance information to construct a distance map 214 of the plate 28, the compressed breast 52 and the biopsy device 102. With this distance map 214, the controller 32 has accurate positioning data regarding the location of the robotic arm 108, and the end effector 112 and needle 104 relative to the breast 52.

Further, as the imaging procedure has already been performed with the breast 52 in the compressed position on the detector surface 50, and because the breast 52 remains in the same compressed position in which the imaging procedure was performed, the controller 32 has access to the fluoroscopic or digital images or the 3D image dataset constructed from the image data in the imaging procedure. As such, the controller 32 can correlate the position of the ROI in the breast 52 that is to be biopsied with the components of the biopsy device 102, as the position of the biopsy device 102 is also known from the distance map 214. Using this position information, the controller 32 can control the movement of the biopsy device 102 to locate the tip 106 of the needle 104 in the proper position and with the required angulation for insert of the needle 104 to perform the biopsy procedure.

The process of the controller 32 moving the biopsy device 102 into the required location for the performance of the biopsy procedure can be performed autonomously by the controller 32, or in conjunction with an initial manual positioning of the biopsy device, where the controller 32 operates to correct and/or fine tune the positioning of the biopsy device 102 relative to the ROI.

Further, the orientation of the collimator 20 can be automatically adjusted during the biopsy procedure in response to information provided from the distance map 214. For example, in the performance of a biopsy procedure, on many occasions a sample of the biopsied tissue obtained by the biopsy device 102 is positioned within a holder (not shown) disposed within a dedicated specimen area on the detector surface 50. These specimen areas are aligned with openings in a sample imaging blade (not shown) movably disposed on the radiation source 16 to limit emission of radiation, e.g., X-rays, front he source 16 through the openings in the sample imaging blade. When a holder is detected on the detector surface 50 by the sensing device(s) 200/ToF sensor (s) 206, the imaging blade can be automatically moved by the controller 32 over the source 16 to limit or focus the emission of X-rays from the source 16 onto the specimen areas containing the sample holder and biopsy samples contained therein for analysis of the samples, without unnecessarily providing an additional radiation dose to the breast 52. Conversely, when the sample holder is removed, the sensing device(s) 200/ToF sensor(s) 206 detect the absence of the holder, and the controller 32 can move the sample imaging blade to a retracted position, thereby allowing a full emission field from the source 16 onto the detector 18.

In addition, prior to performing a biopsy procedure, one or more pre-shot x-ray images are taken of the breast 52 using the radiation source 16 and detector 18 to confirm the location of the ROI initially identified in the fluoroscopic or digital images or the 3D image dataset. With regard to these pre-shot images, the sensing device(s) 200/ToF sensors(s) 206 positioned on or adjacent the radiation source 16, such as on the collimator, can be operated to detect the current position of the collimator and to reposition the collimator relative to the ROI to obtain the desired pre-shot or scout images to confirm the location of the ROI within the breast 52. Similarly to other embodiments of the operation of the distance and location sensing system 201, the distance an position/location information obtained by the sensing device (s) 200/ToF sensor(s) 206 can be employ by the controller 32 in an automatic manner to adjust the position of the collimator, or can be combined with an initial manual positioning to fine tune and/or correct the initial position.

Figure 14:
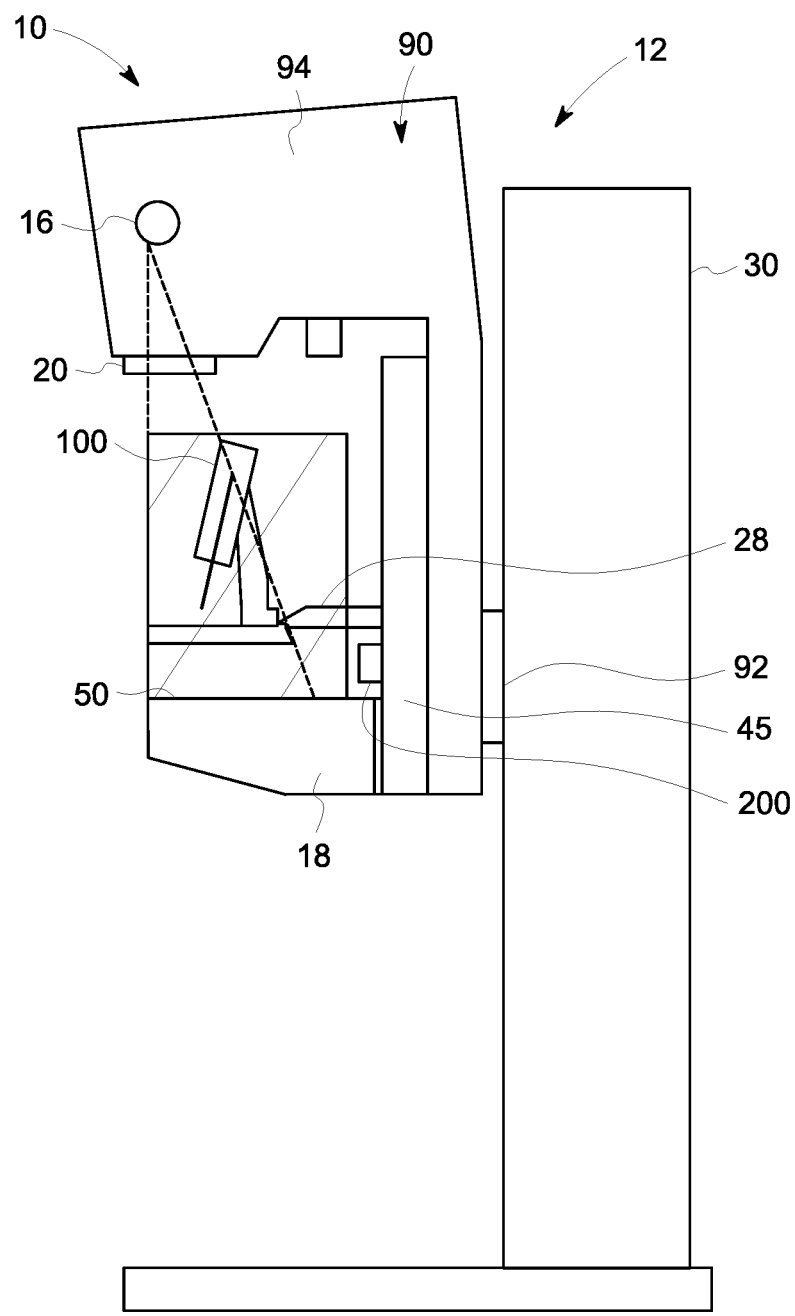
FIG. 14 is an isometric view of another embodiment of the mammography system of FIG. 5, including a biopsy device in accordance with another embodiment of the disclosure.
Figure 15:
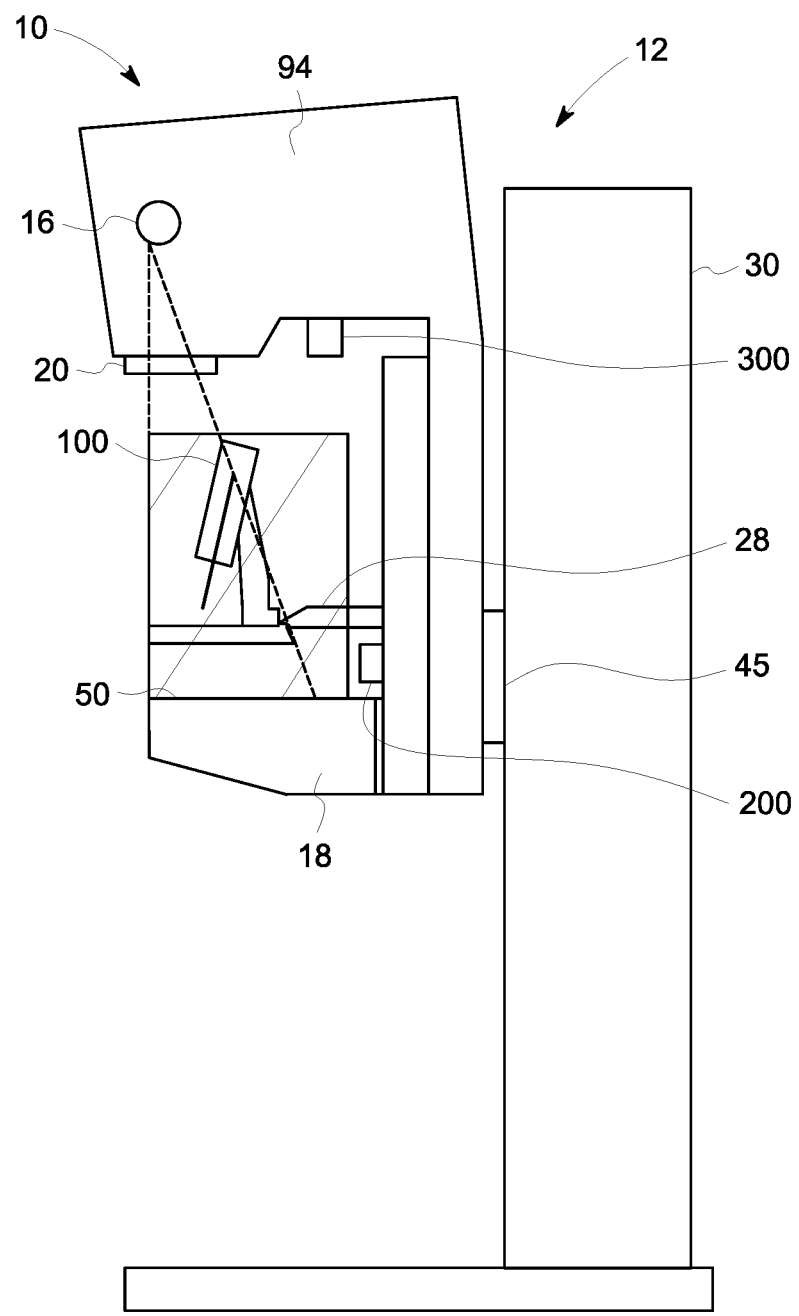
FIG. 15 is an isometric view of another embodiment of the mammography system of FIG. 6, including a biopsy device in accordance with another embodiment of the disclosure.

Further, as shown in the exemplary embodiment of FIGS. 14 and 15, to enhance the ability of the distance and location sensing system 201 to provide accurate distance and position information, multiple combinations of sensing device(s) 200/ToF sensor(s) 206 can be positioned in different locations on the imaging system/device 10 to provide distance data from multiple angles for more a accurate rendering and/or representation of the spatial locations of the compression plate 28, breast 52 and biopsy device 102 relative to one another on the imaging system/device 10.

With the use of the distance and location sensing system 201 on the imaging system/e 10 to provide accurate distance and position information from the sensing device(s) 200 constituting the system 201, a variety of benefits in relation to prior art vision detection and location systems are achieved.

Initially, the sensing device(s) 200 employed in the distance and location sensing system 210 are much less complex in construction and operation than the cameras utilized in prior art vision systems. In particular, the sensing devices 200 only measure the elapsed time between the emission of the wave or radiation from the sensing device 200 and the detection of the reflected wave or radiation. As such, the structural components required for the sensing device 200 to function are much less complex and less costly than for video and still cameras. Further, the distance data, in the form of the elapsed time between emission and detection, is significantly easier to use computationally to arrive at the distance data supplied to the controller 32 for controlling the operation of the various components of the imaging system/ device 10.

In addition, as a result of the simpler construction and data complexity of the sensing device(s) 200, the distance and location sensing system 201 can be integrated into existing and new imaging systems/devices 10 in a much easier and less costly manner.

Further, the use of the waves and radiation emitted by the sensing device 200 to obtain the distance data are much less susceptible to interference from ambient light conditions, as is the case with cameras which require significant ambient light to adequately capture the required visible spectrum images and/or video.

Finally, from the standpoint of patient comfort, the distance and location sensing system 201 does not record any images and/or video of the patient 57 in any state of undress due to the manner in which the distance data is obtained, i.e., through the use of reflected waves and radiation, rather than visible spectrum images or video. Thus, the entire lack of any images of any type of the patient in a state of undress during the entire imaging and biopsy procedure greatly reduces any patient anxiety with regard to the performance of the imaging and biopsy procedures utilizing the imaging system 10 employing the distance and location sensing system 201.

Finally, it is also to be understood that the system 10 may include the necessary electronics, software, memory, storage, databases, firmware, logic/state machines, microprocessors, communication links, displays or other visual or audio user interfaces, printing devices, and any other input/ output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for determining a relative distance between an object to be imaged and one or more components of an imaging system, the method comprising the steps of:
   a. providing an imaging system comprising:
      i. a gantry movably disposed on a support surface and including a radiation source, a detector alignable with the radiation source, the detector having a surface on which an object to be imaged is adapted to be positioned;
      ii. a controller operably connected to the gantry to control the operation of the radiation source and detector to generate image data in an imaging procedure performed by the imaging system, the controller including a central processing unit and interconnected database for processing the image data from the detector to create images, a display operably connected to the controller for presenting information to a user, and a user interface operably connected to the controller to enable user input to the controller; and
      iii. a distance and location sensing system disposed on the gantry and operably connected to the controller the distance and location system including at least one sensing device operable to generate distance data concerning the object;
   b. positioning the object on the surface between the radiation source and the detector;
   c. operating the at least one sensing device to generate the distance data regarding a distance of the object from the at least one sensing device,
   d. determining a position of the object on the surface to determine the position of the object relative to the surface; and
   e. optionally adjusting operation of one or more components of the imaging system based on the position of the object on the surface,
wherein the imaging system is a mammography imaging system including a compression plate disposed on the gantry and movable with respect to the radiation source and the detector, wherein the object is a breast, and wherein the method further comprises the steps of:
   f. operating the at least one sensing device to obtain distance data regarding a distance of the compression plate from the at least one sensing device; and
   g. determining a position of the compression plate relative to the breast.

2. The method of claim 1, further comprising the step of adjusting movement of the compression plate relative to the breast after determining the position of the compression plate relative to the breast.

3. The method of claim 2, wherein the step of adjusting the movement of the compression plate comprises slowing the movement of the compression plate towards the object.

4. The method of claim 1, wherein the step of determining the position of the breast on the surface comprises determining a shape of the breast.

5. The method of claim 1, wherein the step of determining the position of the breast on the surface comprises determining a contact area of the breast with the surface.

6. The method of claim 5, wherein the step of determining the contact area comprises the steps of:
   a. determining a first contact area of the breast with the surface prior to contact of the compression plate with the breast; and
   b. determining a second contact area of the breast with the surface after contact of the compression plate with the breast.

7. The method of claim 6, further comprising calculating an estimated pressure on the breast with the second contact area of the breast with the surface.

8. The method of claim 7, wherein the steps of determining the second contact area and calculating the estimated pressure on the breast are performed continuously during compression of the breast.

9. The method of claim 1, wherein the one or more components of the imaging system comprise a biopsy device mounted to the imaging system, and wherein the step of adjusting the operation of the one or more components of the imaging system based on the position of the object on the surface comprises adjusting the operation of the biopsy device.

10. The method of claim 9, wherein the one or more components of the imaging system comprise a collimator mounted to the imaging system, and wherein the step of adjusting the operation of the one or more components of the imaging system based on the position of the object on the surface comprises adjusting the operation of the collimator.

11. The method of claim 1, wherein the step of determining the position of the object on the surface comprises determining a laterality of the object disposed on the surface.

12. The method of claim 1, wherein the at least one sensing device comprises a pair of sensing devices disposed on the gantry.

13. The method of claim 1, wherein the at least one sensing device is a time-of-flight (ToF) sensor.

14. A method for determining a relative distance between an object to be imaged and one or more components of an imaging system, the method comprising the steps of:
   a. providing an imaging system comprising:
      i. a gantry movably disposed on a support surface and including a radiation source, a detector alignable with the radiation source, the detector having a surface on which an object to be imaged is adapted to be positioned;
      ii. a controller operably connected to the gantry to control the operation of the radiation source and detector to generate image data in an imaging procedure performed by the imaging system, the controller including a central processing unit and interconnected database for processing the image data from the detector to create images, a display operably connected to the controller for presenting information to a user, and a user interface operably connected to the controller to enable user input to the controller; and iii. a distance and location sensing system disposed on the gantry and operably connected to the controller the distance and location system including at least one sensing device operable to generate distance data concerning the object;

b. positioning the object on the surface between the radiation source and the detector;

c. operating the at least one sensing device to generate the distance data regarding a distance of the object from the at least one sensing device, d. determining a position of the object on the surface to determine the position of the object relative to the surface; and e. optionally adjusting operation of one or more components of the imaging system based on the position of the object on the surface, wherein the imaging system is a mammography imaging system including a compression plate disposed on the gantry and movable with respect to the radiation source and the detector, wherein the object is a breast, and wherein the method further comprises the steps of:

f. operating the at least one sensing device to obtain distance data regarding a distance of the compression plate from the at least one sensing device; and g. determining a position of the compression plate relative to the breast, wherein the step of determining the position of the breast on the surface comprises determining a shape of the breast; and wherein the method further comprises the steps of:

h. determining a configuration of the compression plate; and i. comparing the shape of the breast to the configuration of the compression plate to determine compatibility of the compression plate with the breast.

15. A mammography system comprising:

a. a gantry including radiation source, a detector alignable with the radiation source, and a compression plate moveable relative to the detector to secure a patient breast therebetween;

b. a controller operably connected to the gantry to control the operation of the radiation source and detector to generate image data, the controller including a central processing unit and interconnected database for processing the image data from the detector, a display operably connected to the controller for presenting information to a user, and a user interface operably connected to the controller to enable user input to the controller; and c. a distance and location system disposed on the gantry and operably connected to the controller, the distance and location system including at least one sensing device operable to generate distance data regarding the breast disposed on the detector and to guide the movement of the compression plate to compress the breast on the detector, wherein the at least one sensing device comprises at least one pair of sensing devices operable to generate distance data regarding positions of the compression plate, the breast and the detector relative to each other.

16. The mammography system of claim 15, wherein the at least one sensing device is mounted to the gantry on or adjacent the detector, on or adjacent the radiation source, on or adjacent the compression plate, or combinations thereof.

17. The mammography system of claim 15, further comprising a biopsy device mounted to the gantry and operably connected to the controller to control operation of the biopsy device in an interventional/biopsy mode for the mammography system, the biopsy device including a movable robotic arm secured to the gantry, an end effector disposed on the robotic arm opposite the gantry, and a needle operably connected to the end effector opposite the robotic arm wherein the biopsy device is mounted to the compression plate, and wherein the at least one sensing device is operable to generate the distance data regarding the breast disposed on the detector and to guide movement of the biopsy device to perform a biopsy procedure on the breast positioned on the detector.

18. The mammography system of claim 15, wherein the controller is configured to control the movement of the compression plate in response to the distance data for the positions of the compression plate, the breast and the detector relative to each other.

19. The mammography system of claim 15, wherein the controller is configured to employ the distance data for the positions of the compression plate, the breast and the detector relative to each other to compute at least one of a breast shape, a 3D breast image, a speed of movement of the compression plate, a pressure exerted on the breast, and combinations thereof and to control the movement of the compression plate in response to the at least one of the breast shape, the 3D breast image, the speed of movement of the compression plate, the pressure exerted on the breast, and combinations thereof.

20. The mammography system of claim 15, wherein the at least one sensing device is a time-of-flight (ToF) sensing device.

* * * * *